US009526858B2

(12) United States Patent
Zuyderhoudt

(10) Patent No.: US 9,526,858 B2
(45) Date of Patent: Dec. 27, 2016

(54) INHALERS AND HOUSING CAPS FOR INHALERS

(75) Inventor: Krijn Franciscus Marie Zuyderhoudt, Leiden (NL)

(73) Assignee: Teva Pharmaceuticals Industries Ltd., Petach Tivka (IL)

( * ) Notice: Subject to any disclaimer, the term of this patent is extended or adjusted under 35 U.S.C. 154(b) by 493 days.

(21) Appl. No.: 13/990,221

(22) PCT Filed: Nov. 30, 2011

(86) PCT No.: PCT/EP2011/006000
§ 371 (c)(1),
(2), (4) Date: Jul. 22, 2013

(87) PCT Pub. No.: WO2012/072249
PCT Pub. Date: Jun. 7, 2012

(65) Prior Publication Data
US 2013/0298907 A1    Nov. 14, 2013

Related U.S. Application Data

(60) Provisional application No. 61/418,083, filed on Nov. 30, 2010.

(51) Int. Cl.
*A61M 15/00* (2006.01)
*A61M 16/20* (2006.01)

(52) U.S. Cl.
CPC ........... *A61M 16/20* (2013.01); *A61M 15/009* (2013.01); *A61M 15/0065* (2013.01); *A61M 15/0096* (2014.02)

(58) Field of Classification Search
CPC .. A61M 16/20; A61M 16/201; A61M 16/204; A61M 16/205; A61M 16/206; A61M 16/208; A61M 15/0096; A61M 15/0065; A61M 15/0066; A61M 15/0068; A61M 15/007; A61M 15/0071; A61M 15/0073; A61M 15/0075; A61M 15/0076; A61M 15/009; A61M 15/0091; A61M 15/0095; A61M 2202/064; A61M 2005/3125; A61M 2005/3126; A61M 5/31568; G06M 1/041; G06M 1/241; G06M 1/248; G06M 1/243; G06M 1/245

(Continued)

(56) References Cited

U.S. PATENT DOCUMENTS 4,969,578 A    11/1990 Gander et al.
5,460,171 A *  10/1995 Pesenti ............. A61M 15/0096
                                                    128/200.14

(Continued)

FOREIGN PATENT DOCUMENTS

CN    1250385    4/2000
EP    2014325    1/2009

(Continued)

OTHER PUBLICATIONS

International Search Report corresponding to PCT/EP2011/006000, dated Mar. 6, 2012.

*Primary Examiner* — Lynne Anderson
*Assistant Examiner* — Elliot S Ruddie
(74) *Attorney, Agent, or Firm* — RatnerPrestia

(57) ABSTRACT

An inhaler for inhalation into the airway of a user, the inhaler having a housing at least partially defining a flow passageway extending through the inhaler from an air inlet to an outlet, the inhaler including a valve for selectively restricting the flow passageway.

48 Claims, 19 Drawing Sheets

(58) Field of Classification Search
USPC ............ 128/200.23, 200.12, 200.14, 200.18, 128/200.19, 203.12, 203.15; 222/23, 30, 222/36, 37, 38, 131, 162, 182, 183, 325, 222/402.13; 604/58, 97.03, 207–211
See application file for complete search history.

(56) References Cited

U.S. PATENT DOCUMENTS

| | | | |
|---|---|---|---|
| 5,904,139 A * | 5/1999 | Hauser | A61M 15/009 |
| | | | 128/200.14 |
| 6,338,338 B1 | 1/2002 | Brace | |
| 6,415,785 B1 * | 7/2002 | Stage | A61M 15/009 |
| | | | 128/200.12 |
| 2008/0185000 A1* | 8/2008 | Schuckmann | A61M 15/0065 |
| | | | 128/203.15 |
| 2008/0210230 A1 | 9/2008 | Lintern | |
| 2008/0283553 A1 | 11/2008 | Cox | |
| 2010/0126502 A1* | 5/2010 | Fink | A61M 16/20 |
| | | | 128/200.21 |

FOREIGN PATENT DOCUMENTS

| | | |
|---|---|---|
| GB | 2061116 | 5/1981 |
| GB | 2323040 | 9/1998 |
| GB | 2450327 | 12/2008 |
| JP | 07504093 | 5/1995 |
| JP | 10267164 | 10/1998 |
| JP | 2001516243 | 9/2001 |
| JP | 2003072816 | 3/2003 |
| JP | 2008532675 | 8/2008 |
| JP | 2009507591 | 2/2009 |
| WO | 9309830 | 5/1993 |
| WO | 9841253 | 9/1998 |
| WO | WO 98/41252 | 9/1998 |
| WO | 2006097746 | 9/2006 |
| WO | 2007031325 | 3/2007 |
| WO | 2008040062 | 4/2008 |
| WO | WO 2008/040062 | 4/2008 |
| WO | 2009128491 | 10/2009 |
| WO | WO 2009/128491 | 10/2009 |

* cited by examiner

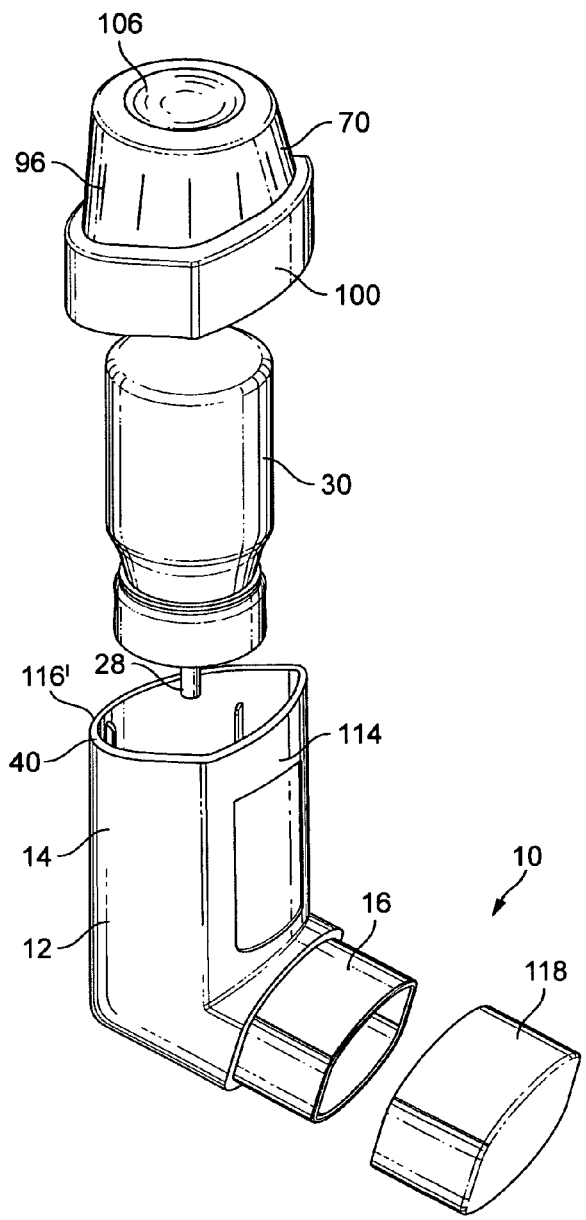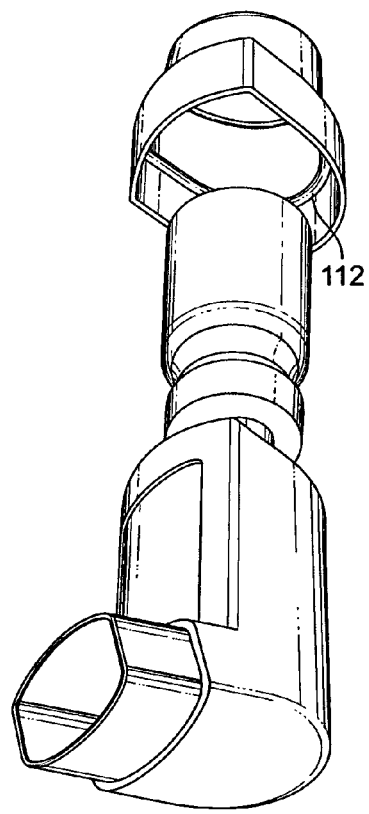
FIG. 7A
FIG. 7B

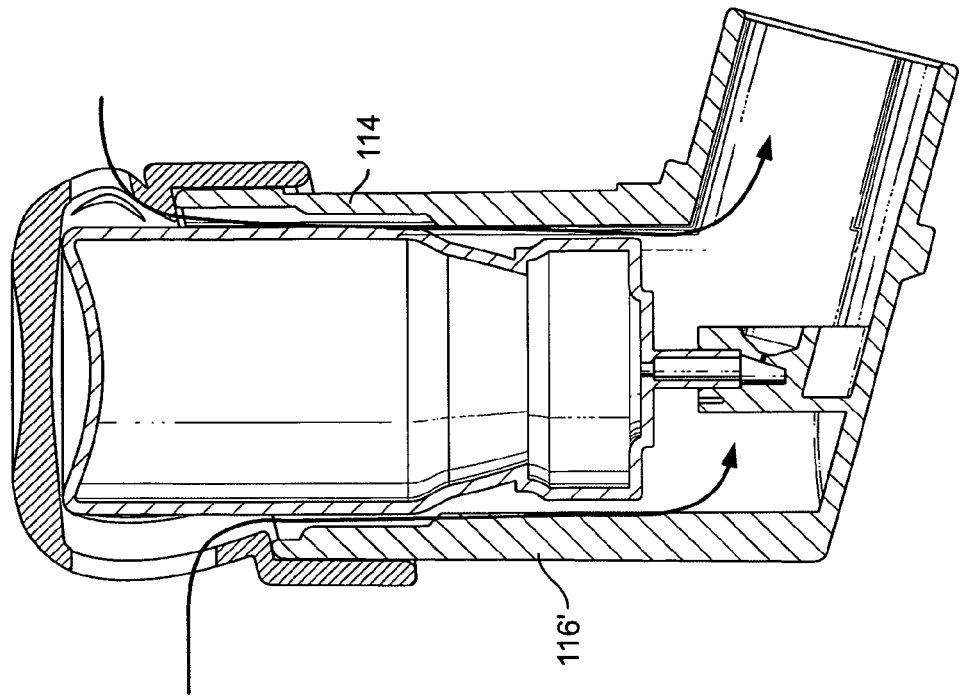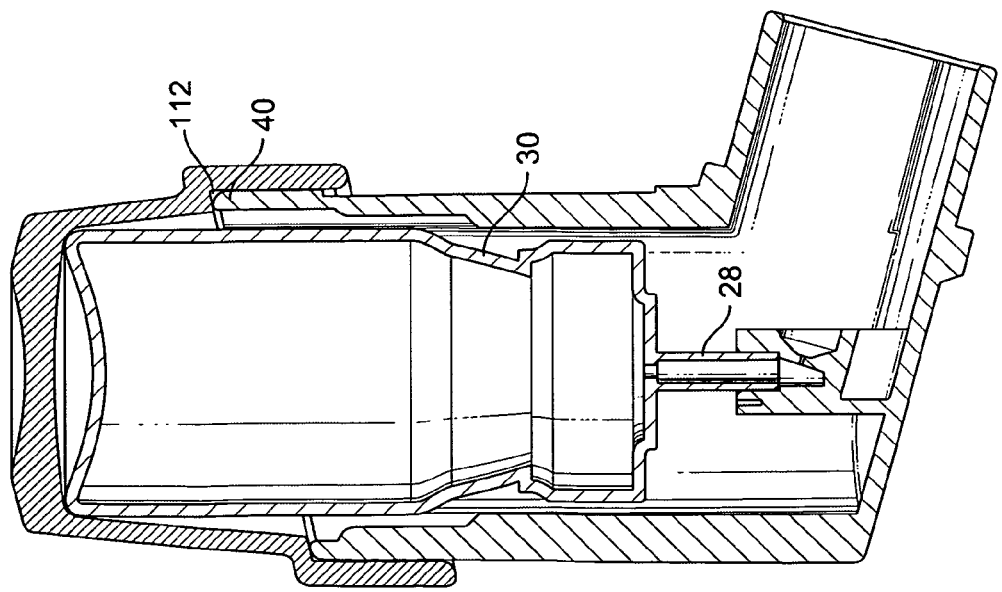

INHALERS AND HOUSING CAPS FOR INHALERS

CROSS-REFERENCE TO RELATED APPLICATION

This is a U.S. National Phase Patent Application of PCT International Patent Application Number PCT/EP2011/006000, filed Nov. 30, 2011, which claims priority benefit of U.S. Provisional Patent application No. 61/418,083, filed Nov. 30, 2010, each of which is incorporated herein by reference in its entirety.

FIELD OF THE INVENTION

The present invention relates to inhalers for inhalation into the airways of users, and to housing caps for inhalers. The invention is applicable in a wide range of inhaler applications, including metered dose inhalers having pressurised metered dose canisters.

BACKGROUND OF THE INVENTION

A known inhaler for inhalation into the airway of a user has a housing at least partially defining a flow passageway extending through the inhaler from an air inlet to an outlet. A pressurised metered dose canister may be placed in the housing and, when a user sucks on a mouthpiece of the housing, air may be drawn into the housing between the canister and an inner wall of the housing and may flow along past the canister towards the outlet. The canister includes a valve stem and a metering valve arranged to seat in a valve stem block formed on the housing and a main canister body of the canister may be moved relative to the housing and valve stem so as to operate the metering valve and fire a metered dose of propellant and active drug through the valve stem block and into the flow passageway.

This type of inhaler often works well, but some users may find it difficult to coordinate an inward breath for inhalation with firing of the canister and, if the canister is fired too early or late relative to an inhalation breath, optimum inhalation may not be achieved.

In WO 2009/128491, which is incorporated by reference herein, a vinyl bag with holes in it is attached to an inhaler body to provide air flow resistance.

In WO 98/41252, which is incorporated by reference herein, an inhaler includes an end cap and housing and the end cap is slideable relative to the housing between a configuration in which there are respective minimum and maximum air flows through the housing. The housing has to be specially formed with a rim and a special collar needs to be located between the housing and end cap and a movement of the collar relative to a dispensing container of the device is undesirably required during an initial setting up of the device. It may also be possible for fluff or debris to become lodged but difficult to sense near the air inlets of the device near the collar, potentially allowing inhalation thereof, and the air inlet area is limited by narrow gaps between the collar and housing.

WO 2008/040062, which is incorporated by reference herein, discloses an inhaler with a cover cap arranged to seal the inhaler so that nothing may enter the inhaler through a housing top in order to exclude mud and dust and for use in wet conditions. The cover cap is flexible to allow operation of the device's canister without allowing mud or dust on the cap to be sucked in and inhaled. However, this requires a complicated arrangement of moving parts elsewhere on the housing in order to provide an air inlet. It is known to provide a breath-actuated inhaler in which the act of inhalation by a user causes a dose to be provided, but this type of device is fairly complicated and expensive.

SUMMARY OF THE INVENTION

The present invention aims to alleviate at least to a certain extent the problems of the prior art.

According to a first aspect of the invention there is provided a housing cap apparatus for an inhaler, the housing cap having a valve for selectively restricting air flow through an air flow passageway of an inhaler. This is advantageous in that the valve can be used to restrict or prevent the user or patient from inhaling at a sub-optimal time relative to drug delivery and may, in particular prevent the user from inhaling substantially too early.

Preferably, at least a portion thereof comprising a deformable portion formed of deformable material and including at least one valve, the deformable portion being deformable between a first configuration in which the valve is restricted and a second configuration in which the valve is open for allowing air flow through an air flow passageway of an inhaler. This is advantageous in that the valve can be used to restrict or prevent the user or patient from inhaling at a sub-optimal time relative to drug delivery and may, in particular prevent the user from inhaling substantially too early. Also, an inhaler using such a housing cap is reliable in its timing of dosing and inhalation, is easy to use and a relatively large valve opening may be achieved with little movement or effort. Additionally a smooth surface area can be provided in the region of the valve which is not likely to accumulate fluff or debris in a position from which it may be inhaled.

The housing cap may have a head portion at least partly formed of deformable material, the valve comprising at least one sealing aperture which is deformable between a closed configuration and an open configuration. The head portion may be formed at least partly of resiliently deformable material for self-closing the sealing aperture to the closed configuration and self-returning the head portion to a rest configuration thereof.

The sealing aperture may be located on an inwardly concave surface of the head portion so as to be biased towards firmer sealing thereof in response to attempted negative inhaling pressure applied inside the head portion. Advantageously, therefore, the sealing arrangement cannot easily be opened just by inhaling with greater force. The sealing aperture may comprise an elongate sealing slit.

The elongate sealing slit may be formed in a sidewall of the head portion.

The sidewall may be generally at least part-cylindrical or at least part-conical when the sealing slit is in the closed configuration. The sidewall may have a lower generally cylindrical portion and an upper generally conical portion and the elongate sealing slit may extend at least partly along each of the generally cylindrical and generally conical portions.

The sidewall may have a curved outwardly convex cross section when the sealing slit is closed. This has the advantage that the sidewall releasably collapses outwardly all around a perimeter thereof as the housing cap is deformed to the open configuration.

The housing cap may include at least one corner and in which at least one said sealing slit is located substantially adjacent and/or aligned extending substantially towards the corner. This configuration has been found to be highly advantageous since it allows substantial opening of the sealing slit in response to little movement of input to the housing cap to open the slit.

A series of said sealing slits may be arranged around the sidewall. In one example, four said sealing slits and four said corners may be provided. This arrangement is highly effective, enabling easy and wide opening of the slits to enable high air flow rates upon inhalation with little resistance due to pressure drop across the valve during proper inhalation. Between four and twenty said slits may be provided in some embodiments, some embodiments having between eight and fifteen said slits, one example having twelve said slits, another having four slits.

When the sealing slit is closed, the head portion may have a generally flat top and the sealing slit may be oriented generally parallel to an axis perpendicular to the generally flat top of the head portion. Accordingly, manual pushing of the head portion along the axis perpendicular to the flat top may open the slit/series of slits.

The generally flat top may be relatively rigid compared to the sidewall. Thus the sidewalls may deform without significant deformation of the flat top. The generally flat top may be: of thicker material than the sidewall, formed of stiffer material than the sidewall (such as being double-shot moulded integrally therewith), or both. Double shot moulding is possible when a stiffer material is used for the top. The extra stiffness of the top prevents undesirable deformation. For example, the centre of the top cannot easily be pushed down to fire the canister without the slits opening properly. The generally flat top may act to spread forces through the slits.

The generally flat top may include an insert formed of stiffer and/or harder material than material of the sidewall.

The sidewall may have a Shore A hardness of about 30, or from about 25 to about 35 Shore A. The generally flat top may have a Shore D hardness of about 40 or less, or from about 35 to about 45 Shore D.

The generally flat top may have a Shore A hardness of about 85, or from about 75 to about 100 Shore A.

The generally flat top may incorporate a central concave finger grip. The finger grip may be surrounded by a chamfer. This encourages the user to push with a central force for good even deformation while also allowing enough room for the user's index finger to operate the housing cap comfortably and helps to align the finger.

The sidewall may be arranged to adopt a deformed bulging configuration (such as an at least part-oblate spheroidal, an at least part-prolate spheroidal or at least part-spherical configuration) when the sealing slit is in the open configuration. With the sidewall cylindrical or conical in the closed configuration, as the head portion is pushed, the sidewall may gradually adopt a generally part-spheroidal configuration and it may transform through a generally part-prolate spheroidal configuration to a generally part-oblate spheroidal configuration or a generally part-spherical configuration as the sealing slit is progressively opened. The head portion may have an engagement portion arranged to engage, move and fire a metered dose canister. Such engagement may be direct or indirect such as via a return spring. The generally flat top may have a lower surface thereof having a downwardly convex central dome surround by a concave annular gutter leading to a downwardly extending cylindrical wall portion. The lower surface may therefore directly mate on top of and engage a metered dose canister with a corresponding mating surface. This advantageously allows a tight fit on the canister, minimising sideways movement if the head portion is pushed sideways, so that apertures/slits cannot be inadvertently deformed and opened without pushing the canister down to fire it.

The engagement portion may comprise a component, such as an insert, the component having a flange of at least partly circular form for engaging a metered dose canister.

The housing cap may include a skirt arrangement arranged to sealingly engage a housing of an inhaler. The slit or series of slits may be spaced from the skirt such that once the housing cap is fixed on the housing (of the inhaler), the slits are spaced from the housing such that when they are opened air may accordingly pass through the slits and into the housing. The skirt arrangement may include a stiffening portion, the stiffening portion having greater stiffness and/or hardness (durometer) than a sidewall portion of the housing cap.

The skirt arrangement may have a shape arranged to fittingly match an end of an inhaler housing in only one relative angular configuration. The shape may have reflection symmetry, such as bilateral symmetry. The shape may have no rotational symmetry.

The housing cap may be removable from the housing, such as by sliding or the provision of mutually engaging threads which permit a threaded twisting removal action for the housing cap. This may therefore advantageously allow cleaning of the housing cap and the housing of any inhaler to which it is attached.

The valve may be operably-connected to a top of the cap such that depression of the top of the cap opens the valve from its closed, rest position. Preferably, the top of the cap is shaped to provide a corner aligned, adjacent or otherwise in communication with the valve, to facilitate opening of the valve. Further preferably, a top of the cap comprises an insert providing a corner aligned, adjacent or otherwise in communication with the valve, to facilitate opening of the valve. Most preferably, a corner per valve is provided, preferably four corners one for each of the four valves. This arrangement is highly effective, enabling easy and wide opening of the slits/valves to enable high air flow rates upon inhalation with little resistance due to pressure drop across the valve during proper inhalation. Preferably, the generally flat top includes a central concave finger grip. The finger grip may be surrounded by a chamfer.

The generally flat top may have a lower surface thereof arranged to mate on top of a metered dose canister. The lower surface may have a downwardly convex central dome surrounded by a concave annular gutter leading to a downwardly extending cylindrical wall portion of the generally cylindrical flat top.

The apparatus may include a skirt arranged to sealingly engage a housing of an inhaler. The cap may be arranged to be connectable to an inhaler housing by provision of mutually engaging threads which permit a threaded twisting removal or connection thereof. A second aspect of the invention provides an inhaler for inhalation into the airway of a user, the inhaler having a housing at least partially defining a flow passageway extending through the inhaler from an air inlet to an outlet, the inhaler including apparatus in accordance with the first aspect of the invention. Preferably, a metered dose canister is located in the housing.

A third aspect of the present invention provides an inhaler for inhalation into the airway of a user, the inhaler having a housing at least partially defining a flow passageway extending through the inhaler from an air inlet to an outlet, wherein a valve is provided for selectively restricting the flow passageway. This is also advantageous in that the valve can be used to restrict or prevent the user or patient from inhaling at a sub-optimal time relative to drug delivery and may, in particular prevent the user from inhaling substantially too early.

The inhaler may further comprise a housing cap apparatus in accordance with the first aspect of the invention.

Preferably, the inhaler having a housing at least partially defining a flow passageway extending through the inhaler from an air inlet to an outlet, the inhaler having a deformable portion formed of deformable material and including at least one valve, the deformable portion being deformable between a first configuration in which the valve is restricted and a second configuration in which the valve is open for allowing air flow through the air flow passageway. This is advantageous in that the valve can be used to restrict or prevent the user or patient from inhaling at a sub-optimal time relative to drug delivery and may, in particular prevent the user from inhaling substantially too early. The deformable portion may comprise at least part of a housing cap, the housing cap being in accordance with the first aspect of the invention. A further aspect of the invention provides an inhaler for inhalation into the airway of a user, the inhaler having a housing at least partially defining a flow passageway extending through the inhaler from an air inlet to an outlet, wherein a valve is provided for selectively restricting the flow passageway. This is also advantageous in that the valve can be used to restrict or prevent the user or patient from inhaling at a sub-optimal time relative to drug delivery and may, in particular prevent the user from inhaling substantially too early.

The outlet may comprise an aperture in a mouthpiece of the housing. The housing may have a canister-receiving portion arranged to receive a metered dose canister.

The inhaler may include a metered dose canister arranged to be located in the canister-receiving portion, the canister having a main body which is movable in the canister-receiving portion for firing a metered dose of drug into the flow passageway.

The canister may have a stem extending from the main body and a metering valve, the main body being pressurised and movable relative to the valve stem for firing the metered dose via the metering valve. Accordingly, a metered dose canister may advantageously be fired at a time when the valve is at a correct moment during or just after the valve for the flow passageway is opened or after the valve begins to open such that good timing and coordination may be achieved.

The valve may be fully closable for fully preventing air flow along the flow passageway. Accordingly a user may be totally unable to inhale through the device when the valve is fully closed and will be prevented from starting an inhalation breath too long before a dose of drug is provided.

The valve may be operable in response to a manual operation so as to permit air flow along the flow passageway. For example, the valve may be operable in response to a manual movement by hand of a metered dose canister received in the housing or by an element such as a housing cap or other actuator mounted to the housing and arranged to act upon such a canister. The canister and the valve may be arranged for coordinated opening of the valve and firing of the metered dose in response to a manual operation, the canister being movable in the housing in response to the manual operation. In this case, the canister may be moveable in the housing in response to the manual operation. This is highly advantageous in that the provision of a drug, such as by way of a metered dose from the canister, may be timed to be at an optimum moment during an inhalation breath.

The valve may include a sealing ring arranged to selectively form a seal between a metered dose canister and an inner wall of the housing. A metered dose canister may be located in the housing, the canister having a cylindrical surface arranged to selectively seal inside the sealing ring. The canister may have neck portion or other formation of smaller cross-dimension, e.g. diameter, than the cylindrical surface and may be slideable in the housing for placing the neck portion adjacent the sealing ring and spaced inwardly therefrom so as to open the valve. In this way, the valve may advantageously be opened at an optimum moment during movement of the canister so as to provide a dose of drug.

A ring may be located in the housing and arranged to steady a canister inside the housing. This may therefore provide excellent sealing at the sealing ring and may assist in providing smooth sliding of the canister relative to the sealing ring. The sealing ring may be flexible and may additionally be arranged to deform from a closed configuration to an open configuration in which it permits airflow along the flow passageway. The inhaler may include a housing cap arranged to fit on the housing, at least part of the housing cap being movable relative to the housing for opening and closing the valve. The housing may have at least one aperture formed in an outer wall thereof and the housing cap may have at least one inlet aperture formed through a wall thereof, the housing cap being moveable relative to the housing to place the apertures in and out of register with one another for opening and closing valve, respectively.

The housing cap may have a skirt arranged to mate around the housing.

The housing cap may be removably attachable to the housing.

Housing caps in accordance with or used in any of the above aspects may advantageously be fitted to an inhaler housing thereby providing a valve for restricting or blocking airflow through the inhaler, such that opening of the valve from a restricted or fully blocking configuration may be coordinated with drug delivery for optimum inhalation. Housing caps with these features may be fitted to a wide range of existing inhaler housing bodies, thereby substantially improving the performance of the same without requiring substantial redesign costs.

Housing caps in accordance with or used in any of the aspects of the invention may have a head portion formed of deformable material, the head portion incorporating the valve, which is in the form of at least one sealing aperture which is deformable between a closed configuration and an open configuration. The housing cap may be so deformable by pressing downwardly on the head portion. The closed configuration may be a relaxed or rest configuration of the head portion and the open configuration may be a deformed configuration thereof, such that the head portion may advantageously be biased towards and return to the closed configuration from the open configuration automatically. The head portion may be formed of resiliently deformable material for self closing the aperture to the closed configuration and/or self-returning the head portion to the rest configuration.

BRIEF DESCRIPTION OF THE DRAWINGS

The present invention may be carried out in various ways and a number of preferred embodiments of inhalers and housing caps in accordance with the present invention will now be described by way of example with reference to the accompanying drawings, in which:

FIGS. 7A to 7F show a further modification of the embodiment of FIGS. 5A to 5F;

DETAILED DESCRIPTION OF THE DRAWINGS

Figure 1B:
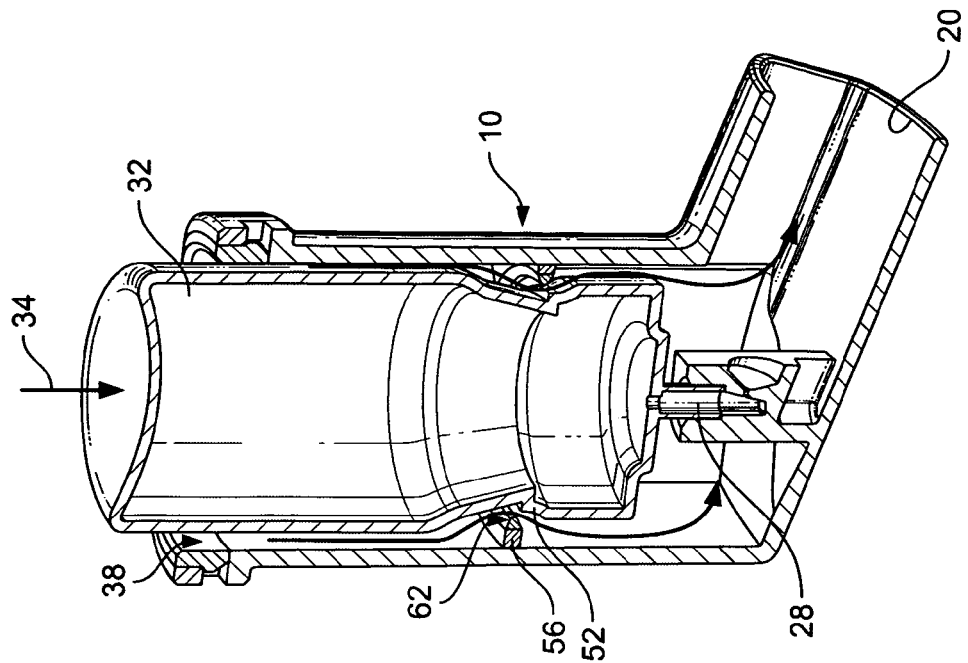
FIGS. 1A and 1B are sections through a first embodiment of an inhaler in accordance with the present invention.
Figure 1A:
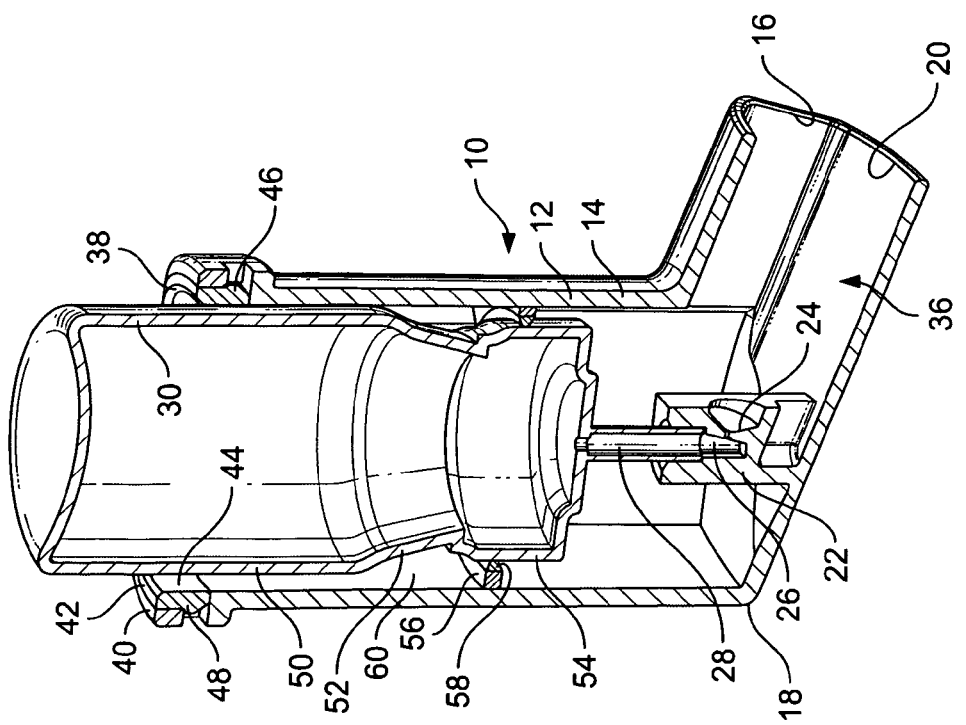

FIGS. 1A and 1B show sectional views through a preferred embodiment of an inhaler 10 in accordance with a preferred embodiment of the present invention. The inhaler 10 has a housing 12 having a hollow main body 14 and a mouthpiece 16 oriented approximately perpendicular to the main body 14 and located at a lower end 18 of the housing 12, the mouthpiece having an aperture 20 forming an outlet from the housing 12. The view in FIG. 1A shows a section through the central plane of the inhaler 10 and therefore only shows a "right side" of the inhaler, the left side of the inhaler being substantially a mirror image. Other embodiments are also shown like this.

The housing 12 is formed with a valve stem block 22 having an outlet nozzle 24 communicating with an inlet passage 26 into which the stem 28 of a metered dose canister 30 may be inserted. The canister 30 has a main body 32 which may be pushed down into the main body 14 of the housing 12 in the direction of the arrow 34 in FIG. 1B so as to operate a metering valve (not shown) of the metered dose canister 30 so as to fire a metered dose of propellant and active drug from the pressurised interior of the main body 32 through the nozzle 24 into a flow passageway 36 leading towards the outlet aperture 20 of the mouthpiece 16, from an air inlet 38 located at a top end 40 the housing 12.

The main body 32 of the metered dose canister 30 is substantially circular in a cross-section transverse to a longitudinal axis thereof and a ring 42 having a circular inner face 44 is press-fitted into a groove 46 formed in the main body 14 of the housing 12 near the top end 40 of the housing 12, with a peripheral tooth 48 of the ring 42 engaging in the groove 46. Although the cross-section of the hollow main body 14 is generally square or four sided with four distinct sidewalls which may each be generally straight or convex in a cross-section transverse to the longitudinal axis of the canister 30 or main body 14 of the housing 12, the circular inner face 44 and a circular main wall 50 of the metered dose canister 30 provide the air inlet 38 in the form of an annular, circular clearance therebetween.

The metered dose canister 30 also has a neck portion 52 of reduced diameter relative to a lower cylindrical sealing portion 54 thereof—also known as a ferrule 54. As shown in FIG. 1A, a valve or sealing ring 56 with a circular inner face or edge 58 is secured to an inner wall 60 of the main body 14 of the housing 12, the inner sealing face 58 sealing against the cylindrical portion 54 of the metered dose canister 30 when the canister 30 is in the rest position shown in FIG. 1A.

Figure 2B:
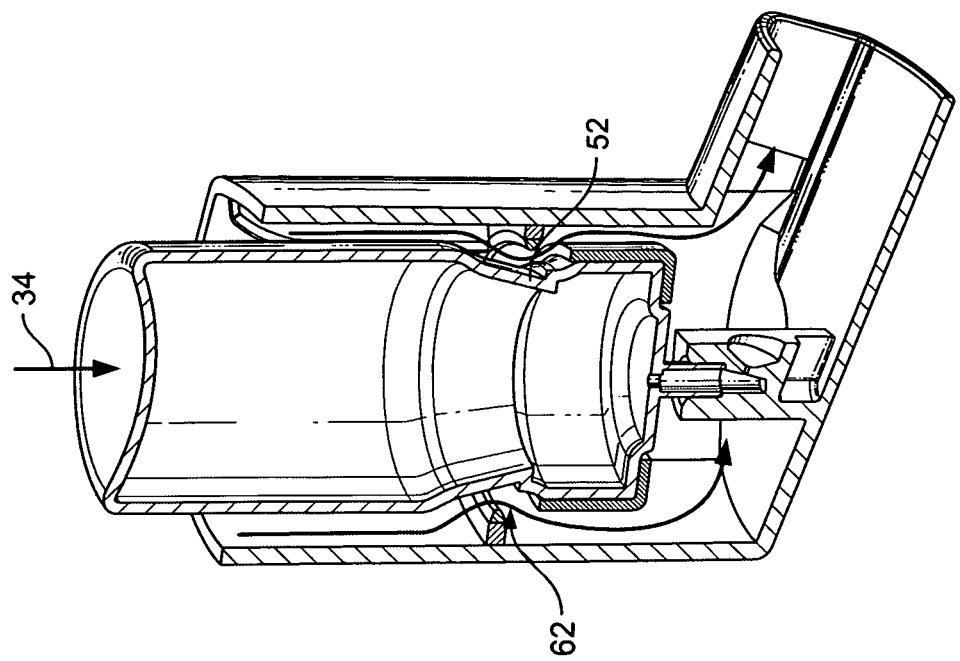
FIGS. 2A and 2B are sections through a second embodiment of an inhaler in accordance with a preferred embodiment of the present invention.
Figure 2A:
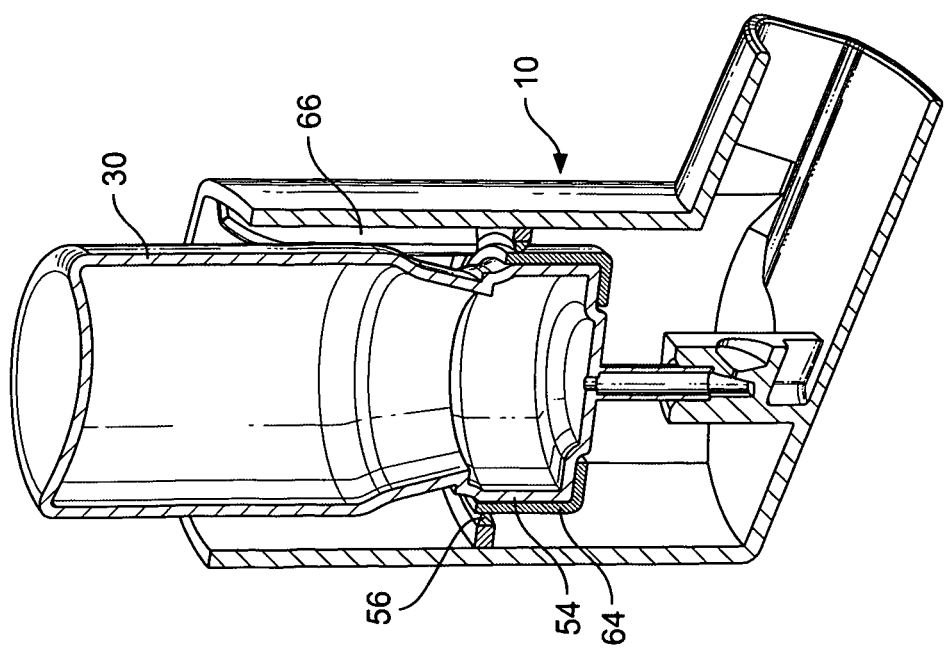

When a user wishes to inhale a metered dose from the inhaler 10, at first, in the configuration of FIG. 1A inhalation is not possible because the airflow passageway 36 is fully blocked by the valve or sealing ring 56 which is in engagement with the canister 30. A sucking action on the mouthpiece 16 therefore does not result in airflow. However, if zero pressure or a slight negative pressure is maintained on the mouthpiece by the user in anticipation of an inward breath, and if the canister 30 is then pushed down into the housing 12, the neck portion 52 of the canister moves down to be adjacent and spaced from the valve or sealing ring 56, with a clearance 62 therebetween, such that flow is permitted along the flow passage 36 from the air inlet 38 past the clearance 62 to the outlet aperture 20 as the users breathes in. At a coordinated point in the opening of the clearance 62 at the valve 56, due to the downward motion of the main body 32 of the canister 30 relative to the valve stem 38, the metered dose canister 30 fires so as to eject propellant and active drug through the nozzle 24 into the flow passageway 36 for inhalation with the air passing along the flow passageway 36. Accordingly, good coordination and timing of the inhalation breath and firing of the canister may be achieved even by users/patients with less than optimum timing coordination. Once the user releases pressure on the canister, the canister returns to the FIG. 1A position automatically by virtual of internal pressure or an internal spring (not shown) tending to extend the valve stem 38. FIGS. 2A and 2B show a modified version of the embodiment of FIGS. 1A and 1B in which the same reference numerals are used to indicate the same or similar components, although in this embodiment, the cylindrical sealing portion 54 of the canister 30 is sealingly seated in an additional sealing ring 64 which seals against the valve 56 when the canister 30 is in the rest position of FIG. 2A. As shown in FIG. 2B, and in a similar way to that shown in FIG. 1B, a clearance 62 is formed between the neck portion 52 of the canister 30 and the valve 56 when the canister 30 and ring 64 are moved down in the direction of the arrow 34 to fire the canister 30. A steadying element 66 or ring 66 is also shown in FIGS. 2A and 2B for maintaining the main body 32 of the canister 30 co-axial with the circular inner face 58 of the valve 56 so as to provide good sealing without jamming of the valve 56 and additional ring 64.

Figure 3A:
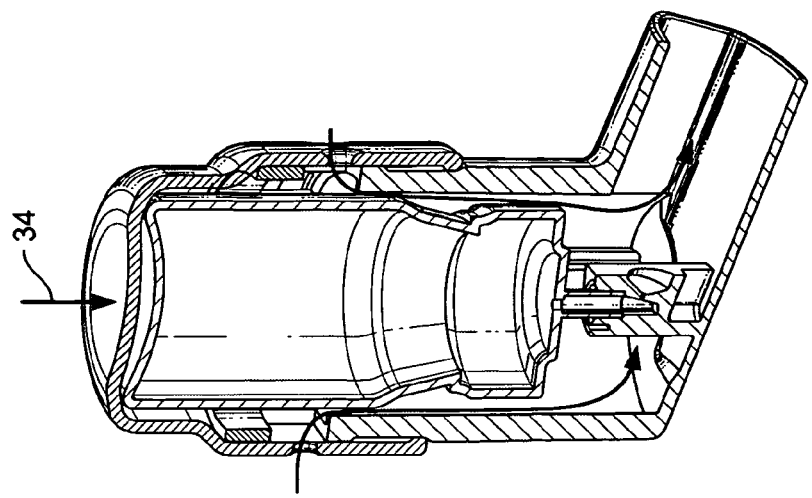
FIGS. 3A, 3B and 3C are sections through a third embodiment of an inhaler in accordance with the present invention and including a housing cap.
Figure 3B:
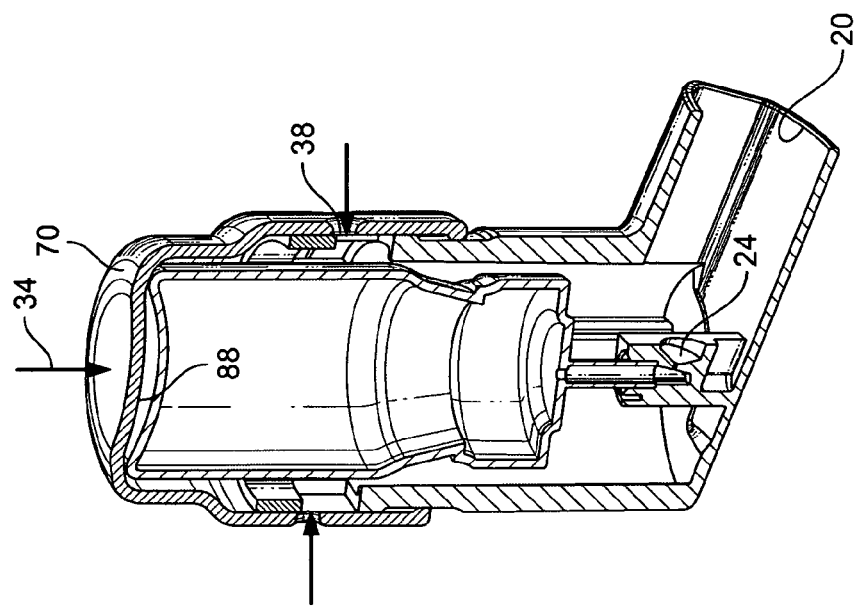
Figure 3C:
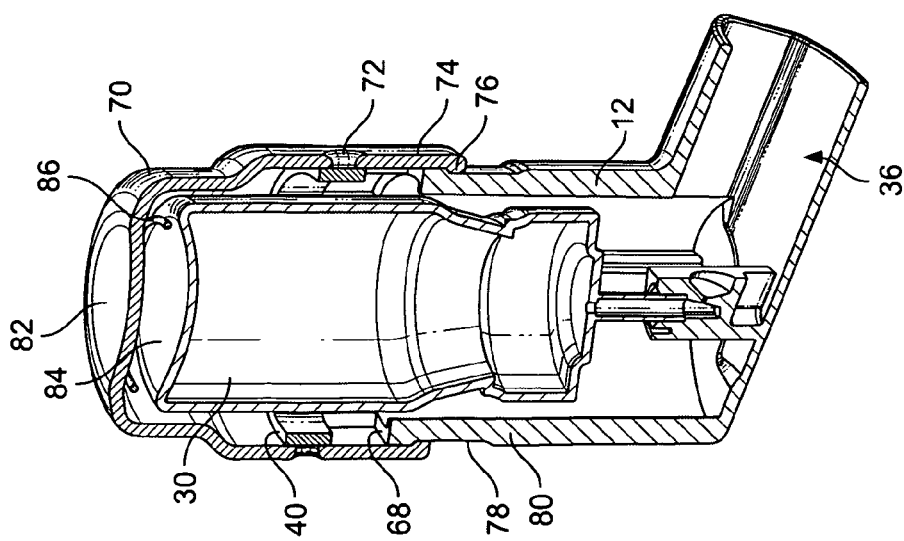

FIGS. 3A to 3C show a modified embodiment in which the same reference numerals are used for the same or similar features to those in FIGS. 1A and 1B. As shown in FIG. 3A, the sealing ring (previously identified with reference 56) is absent, a series of apertures 68 are provided spaced around the main body 14 of the housing 12 near the top end 40 thereof, and a housing cap 70 is provided with a corresponding series of apertures 72 formed in a skirt portion 74 thereof. The skirt portion 74 has a lower rim 76 snap-fitted into and slideable up and down in an annular groove 78 formed in an outer wall 80 of the main body 14 of the housing 12. The housing cap 70 has a head portion 82 which, in the rest configuration of FIG. 3A, is maintained spaced apart from a top surface 84 of the dose canister 30 by a return spring 86. The canister 30 has internal pressure and/or a spring (not shown) in the metering valve (not shown) thereof which biases the canister 30 and therefore its top surface 84 up to the position of FIG. 3A, with the spring 86 thereby biasing the head portion 82 and entire housing cap 70 to the position shown in FIG. 3A in which the apertures 72 and apertures 88 are not in register and the housing cap 70 is therefore sealed to the main body 14 thereby blocking the passageway 36 through the housing 12. When a user wishes to inhale a metered dose, as shown in FIGS. 3B and 3C, pushing down on the housing cap 70 causes a direct or indirect (via the spring 86) engagement of a lower engagement surface 88 of the head portion 82 of the housing cap 70 with the canister 30, such that full movement of the housing cap 70 to the fully lowered configuration of FIG. 3C in which the rim 76 can move no further along the groove 78 fires the canister 30. It will also been seen from FIG. 3B that the apertures 72 and 68 begin to come into register with one another such that they collectively form the air inlet 38 into the housing 12 and allow flow through the flow passageway 36 past the nozzle 24 to the outlet aperture 20. Therefore, in accordance with the timing/coordination provided by this embodiment, the air inlet 38 may begin to be opened by the apertures 72, 68 coming into register slightly before the canister 30 is fired, thereby ensuring a slightly "mid-stream" firing of the canister 30 into the inhaled breath of the user. After use, the housing cap 70 and canister 30 automatically return to their FIG. 3A positions.

Figure 4A:
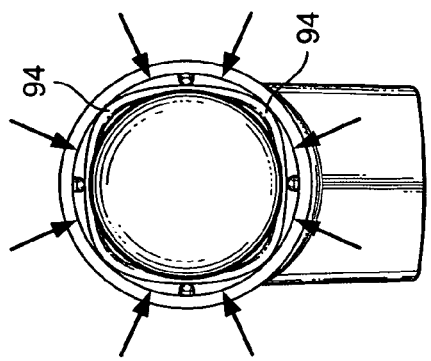
FIGS. 4A and 4B, 4C and 4D are views of a fourth embodiment of an inhaler in accordance with the present invention.
Figure 4B:
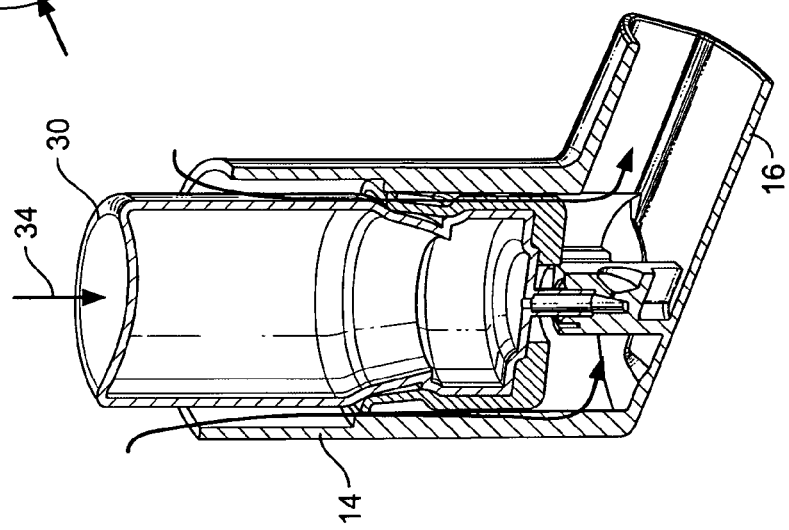
Figure 4C:
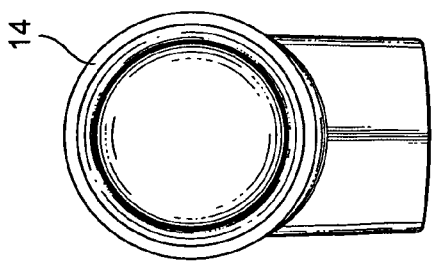
Figure 4D:
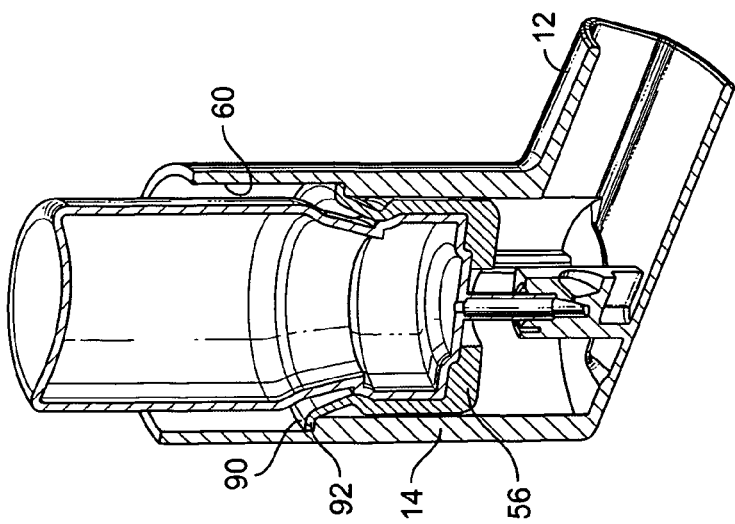
Figure 5C:
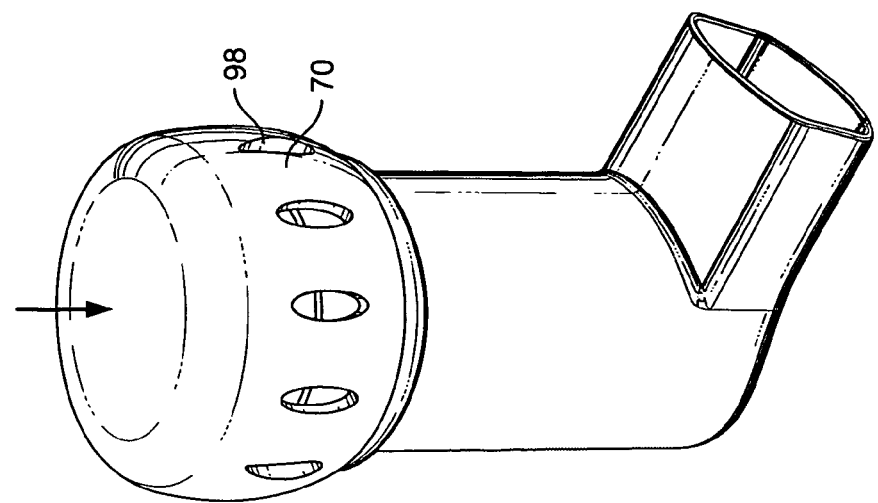
FIGS. 5A to 5F are views of a fifth preferred embodiment of an inhaler in accordance with the present invention and including a housing cap.
Figure 5B:
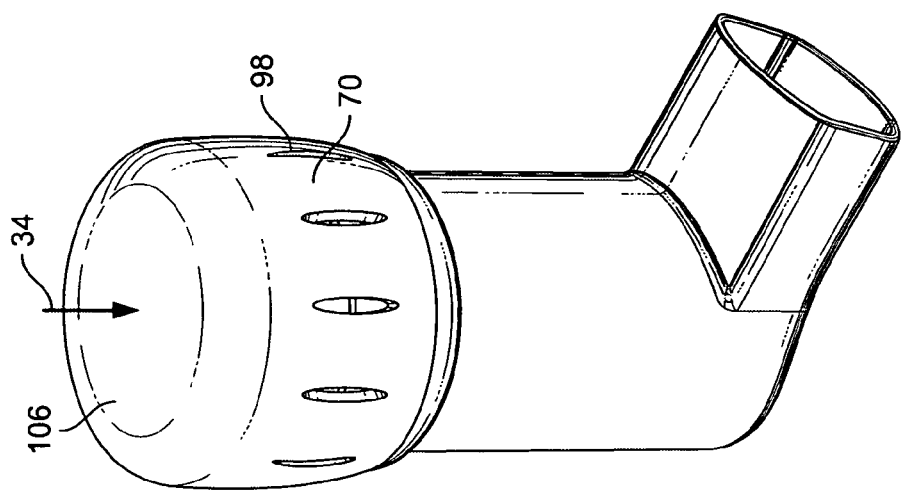
Figure 5A:
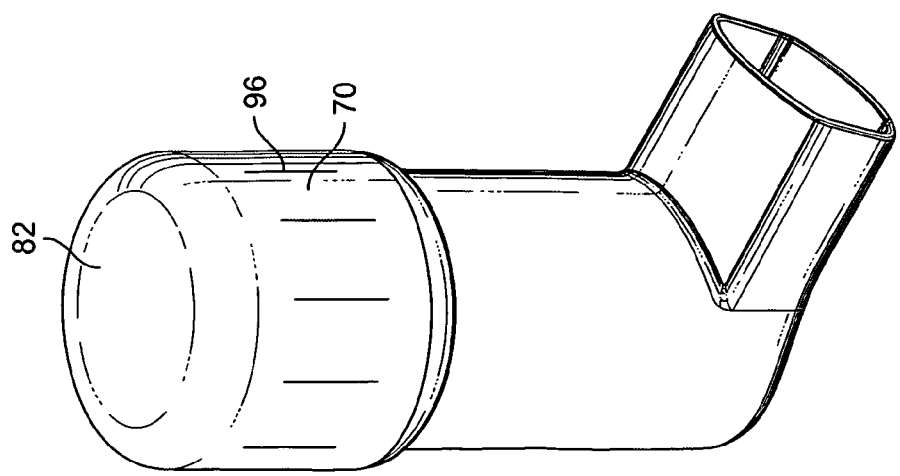
Figure 5F:
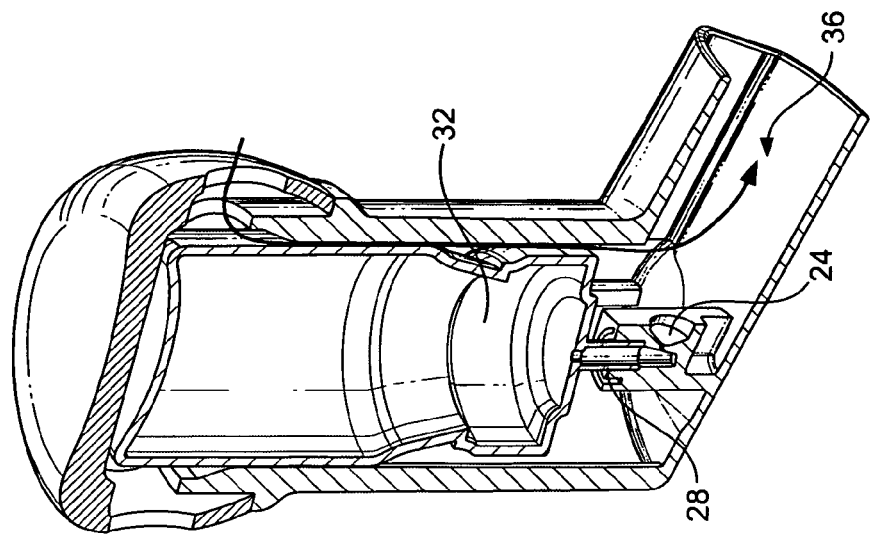
Figure 5E:
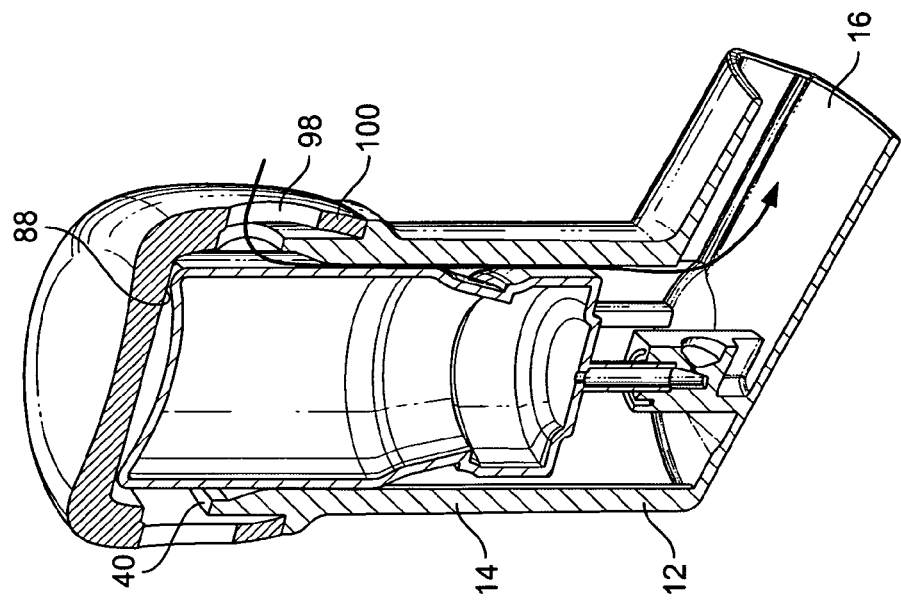
Figure 5D:
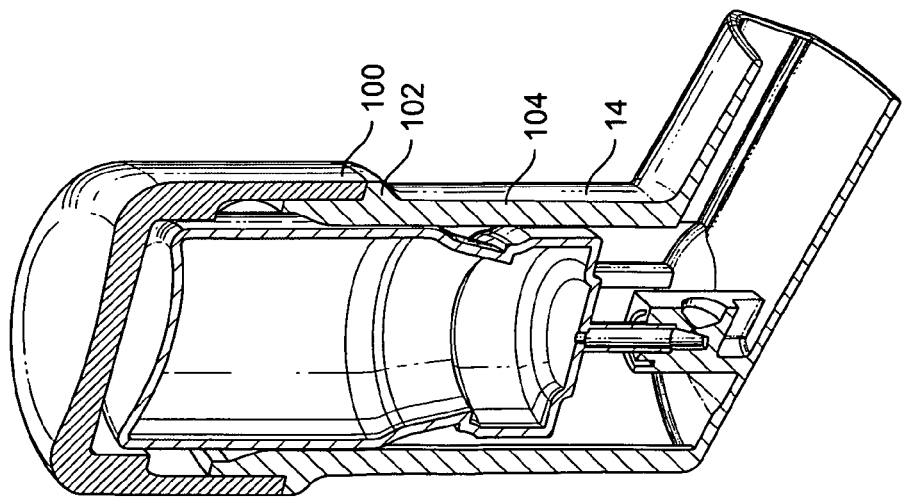
Figure 6C:
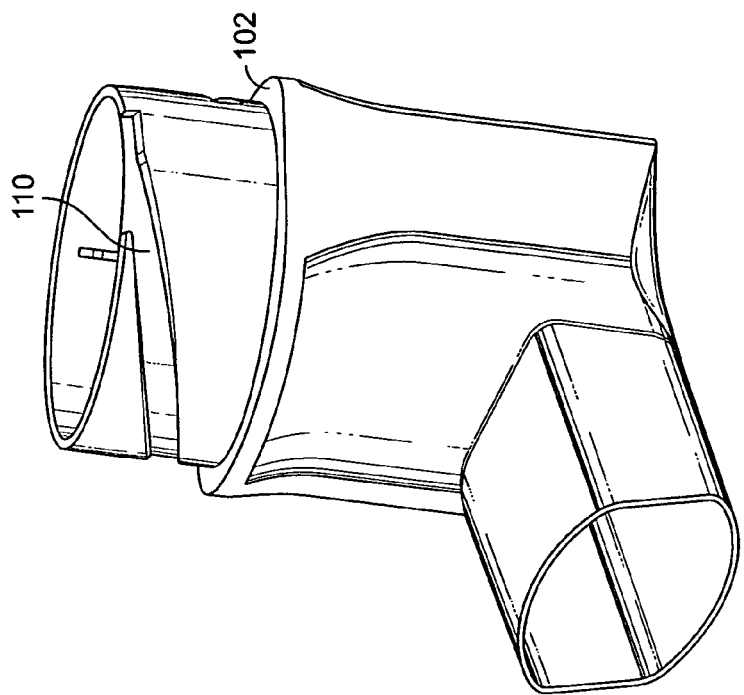
FIGS. 6A to 6G show a modification of the embodiment of FIGS. 5A to 5F.
Figure 6B:
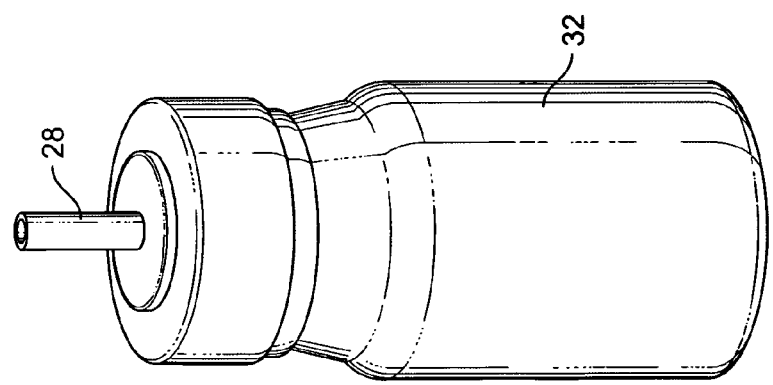
Figure 6A:
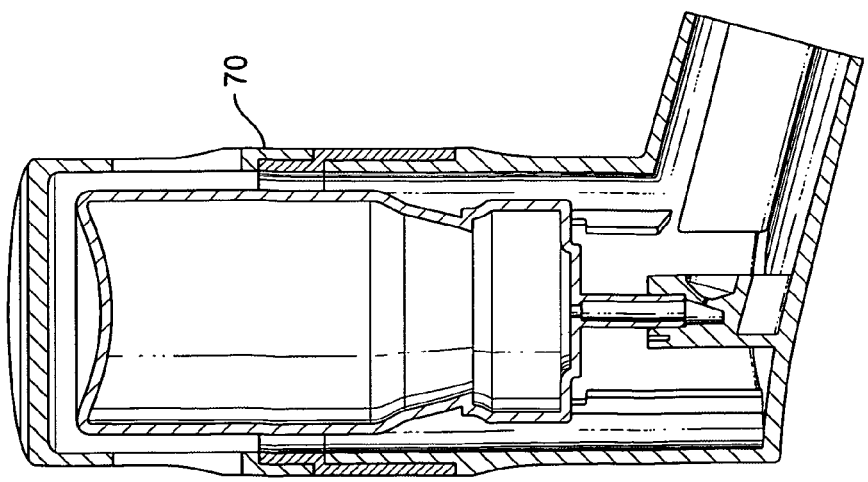
Figure 6F:
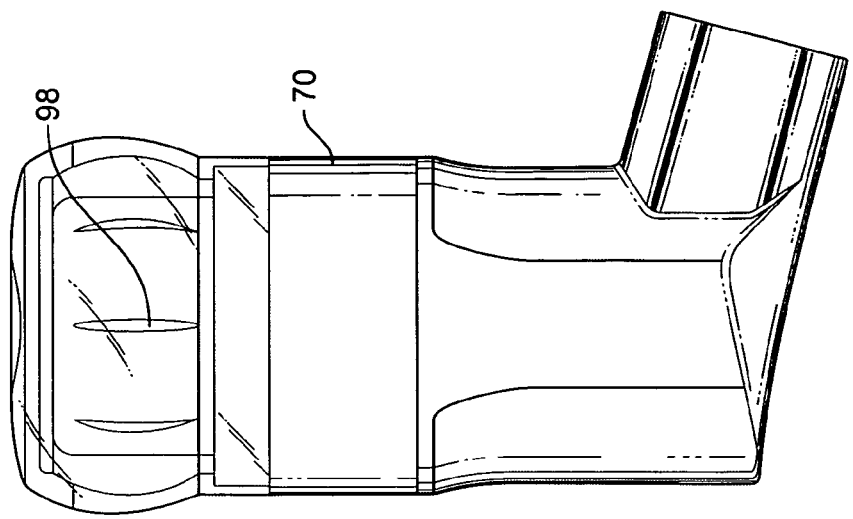
Figure 6E:
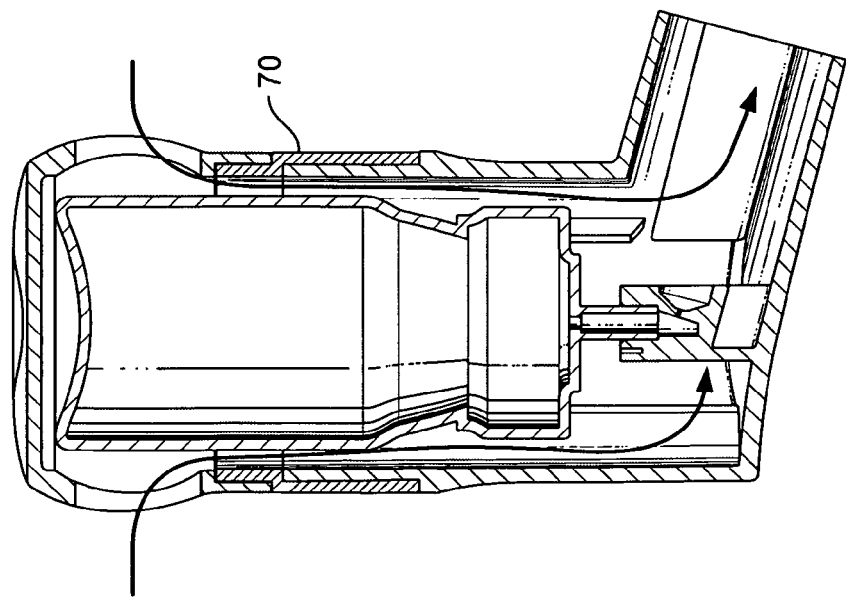
Figure 6D:
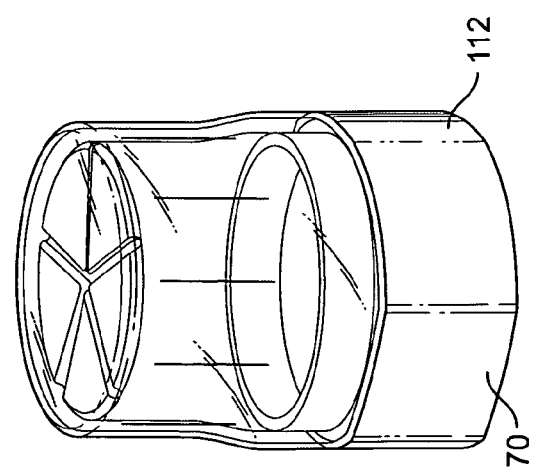
Figure 6G:
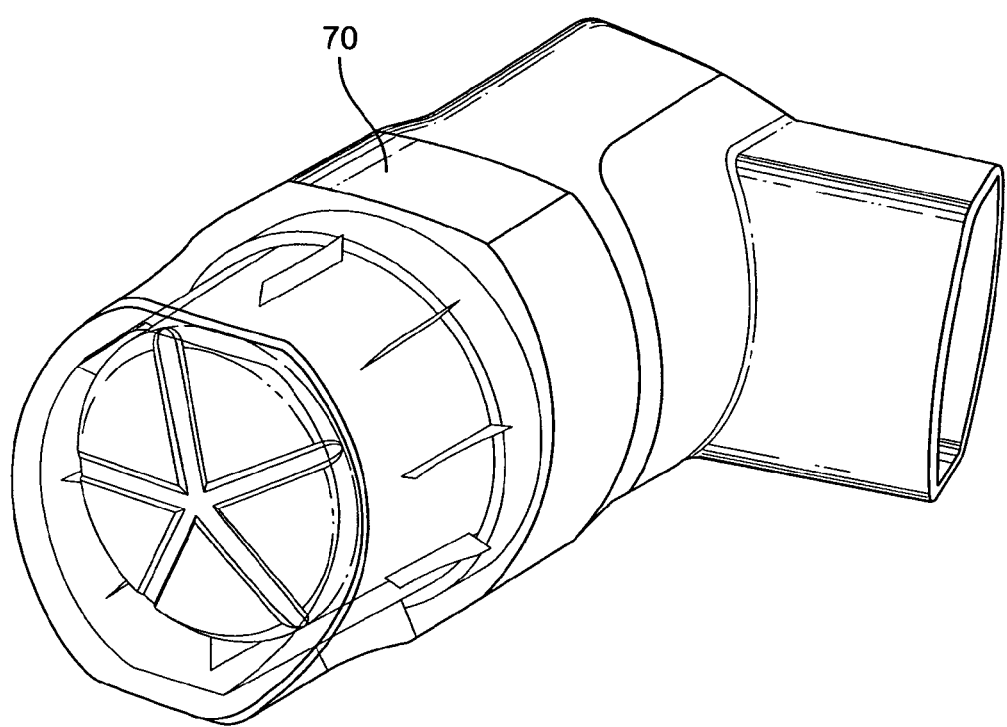
Figure 7D:
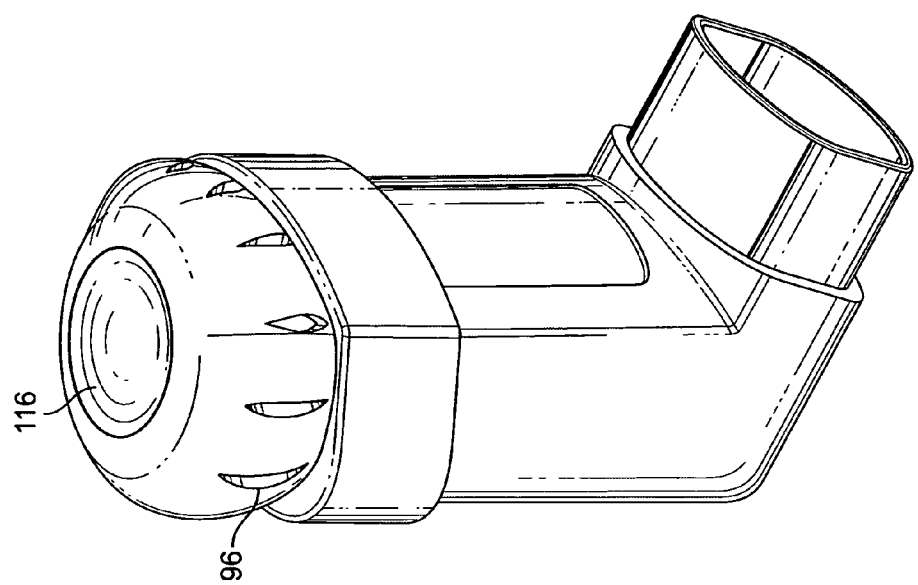
Figure 7C:
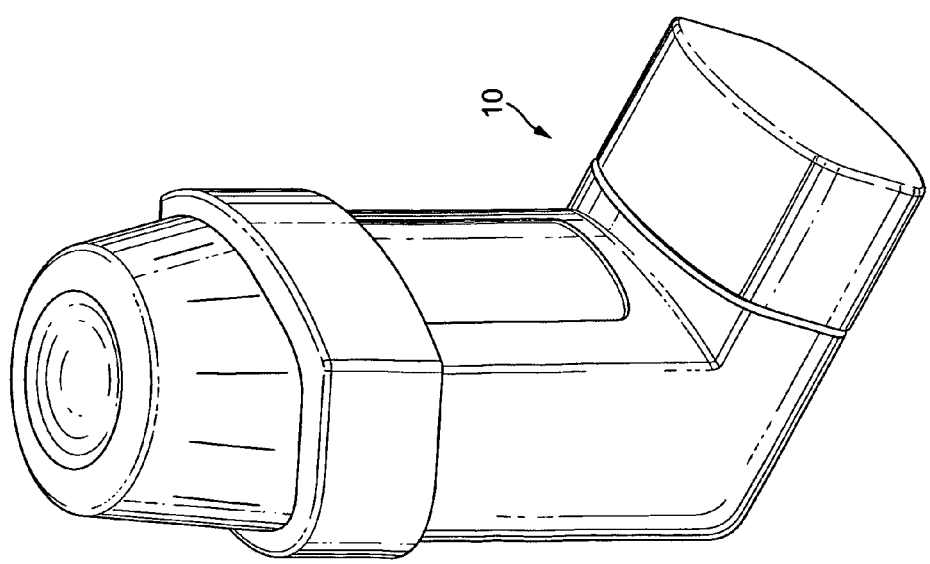

FIGS. 4A to 4D show a modified version of the embodiment of FIGS. 1A and 1B in which similar reference numerals are used to denote the same or similar features. As shown in FIG. 4A, the sealing ring (previously identified as reference 56) is replaced by a valve in the form of a flexible seal 56, which is bucket shaped, having an upper rim 90 seated on a ledge 92 formed on the inner wall 60 of the main body 14 of the housing 12. As shown in FIG. 4B, the main body 14 in this embodiment is generally cylindrical. The canister 30 seals in the flexible seal 56 and the upper rim 90 of the seal 56 seals on the ledge 92 thereby blocking the flow passageway 36. As shown in FIG. 4D, the rim 90 is secured to the inner wall 60 in four places 94, and when the canister 30 is pushed in the direction 34, the seal is broken between these places, thereby allowing airflow between the inner wall 60 and the seal 56 such that inhalation through the mouthpiece 16 may be achieved when the canister 30 is pressed into the main body 14. FIGS. 5A to 5F show a modified embodiment similar to that in FIGS. 3A to 3C and in which the same reference numerals are used to denote the same similar features, and in which the housing cap 70 is made of deformable material. In particular, the housing cap 70 has a head portion 82 with a deformable sidewall 96, the sidewall having a series of twelve vertically oriented slits 98 which are closed in the configuration of FIGS. 5A and 5D but which progressively open through the configuration of FIGS. 5B and 5E to the configuration of FIGS. 5C and 5F, the slits being spaced around the sidewall 96. As shown in FIGS. 5D and 5E, the slits 98 are positioned at least partially above the top end 40 of the main body 14 of the housing 12 and the lower skirt portion 100 of the housing cap 70 is positioned below the slits 98 and sealingly engages on a circumferential step 102 projecting from an outer wall 104 of the main body 14.

When a user wishes to inhale a metered dose from the canister 30 the user may first apply zero pressure or a slight negative pressure to the mouthpiece 16 in anticipation of inhaling a breath therethrough. The user may then progressively press down on the head portion 82 of the housing cap 70 and FIGS. 5B and 5E show a partially depressed configuration in which the sidewall 70 adopts a part-prolate spheroidal configuration in which it is deformed such that the slits 98 are partially opened and the user may begin to inhale a breath. The user progressively presses down upon and moves a generally flat top surface 106 of the head portion 82 downwardly and a lower engagement portion 88 thereof presses down upon and begins to move the canister main body 32 downwardly relative to the valve stem 28 such that in a configuration at that shown in FIG. 5C or 5F, or slightly before it, the canister fires a metered dose of propellant and drug through the nozzle 24 into the flow passageway 36. As shown in FIG. 5C, with the top surface 106 pushed further down as shown in FIG. 5C, the sidewall 70 adopts a more deformed configuration in which it has a generally part-spherical or may have a part-oblate spheroidal shape in which the slits 98 are opened wider than in FIG. 5B. Accordingly the gradual opening of the slits 98 and the coordinated timing of the firing of the canister 30 may provide very good timing for metered dose inhalation.

FIGS. 6A to 6G show an embodiment similar to that in FIGS. 5A to 5F, but in which the housing 12 is provided with a thread 110 for threaded engagement with a corresponding thread (not shown) in the housing cap 70. Thread 110 is clockwise to tighten, as shown in this example. Twisting of the housing cap 70 in an anticlockwise direction may accordingly allow removal of the housing cap 70 for washing of the various components.

FIGS. 7A to 7F show a modified version of the embodiment of FIGS. 5A to 5F in which the main body 14 of the housing 12 has a non-circular cross-section in a plane perpendicular to a longitudinal axis thereof and of the canister 30. The top end 40 of the housing is also truncated at a slanted angle relative to this plane. Accordingly, the skirt 100 is provided with an internal ledge 112 and the skirt 100 is adapted to snugly slide over the main body 14 and seal onto it with the ledge 112 sealing on top of the top end 40 of the main body 14. The sidewall 96 generally tapers towards the generally flat top surface 106 in a conical fashion, although may be cylindrical in other embodiments. The sidewall 96 includes approximately twelve slits 98 of differing lengths (see FIG. 7F), with those near a higher front wall 114 of the main body 14 being shorter than those nearer a lower rear wall 116' of the main body 14. The generally flat top surface 106 has a central concave dimple 116 which may be of assistance in locating a user's thumb or finger thereon for operation of the inhaler 10.

When a user wishes to inhale through the inhaler 10, a zero or slightly negative pressure may be applied to the mouthpiece cover 16 and the user may press down on the dimple 116 thereby deforming the sidewall 96 so as to gradually open the slits 98 and causing the canister 30 to fire at an appropriate time, e.g. mid-stream or fairly early, during the inhalation breath. When the inhaler 10 is to be stored out of use, a mouthpiece cap 118 may be applied to the mouthpiece 16, which, with the housing cap 70 in place enables the housing 12 to be substantially fully sealed closed. The housing cap 70 and/or mouthpiece cap 118 may be removed for washing the various components. The mouthpiece cap may include a vent for preventing trapping of humidity inside the inhaler. The resilient nature of the sidewall 96 in this embodiment and in the embodiments of FIGS. 5A to 5F and 6A to 6G ensure that once the inhalation breath has been completed and the user relaxes pressure on the housing cap, the housing cap returns to the undeformed configuration of FIGS. 7A, 5A and 6A, respectively.

Figure 8C:
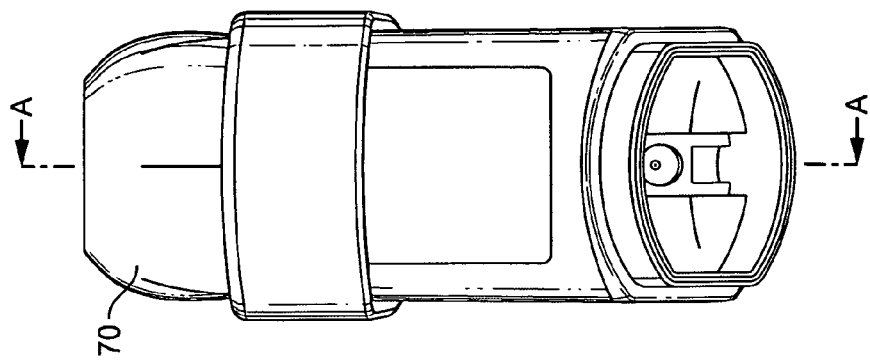
FIGS. 8A to 8H show various views of a modified version of the embodiment of FIGS. 7A to 7F.
Figure 8B:
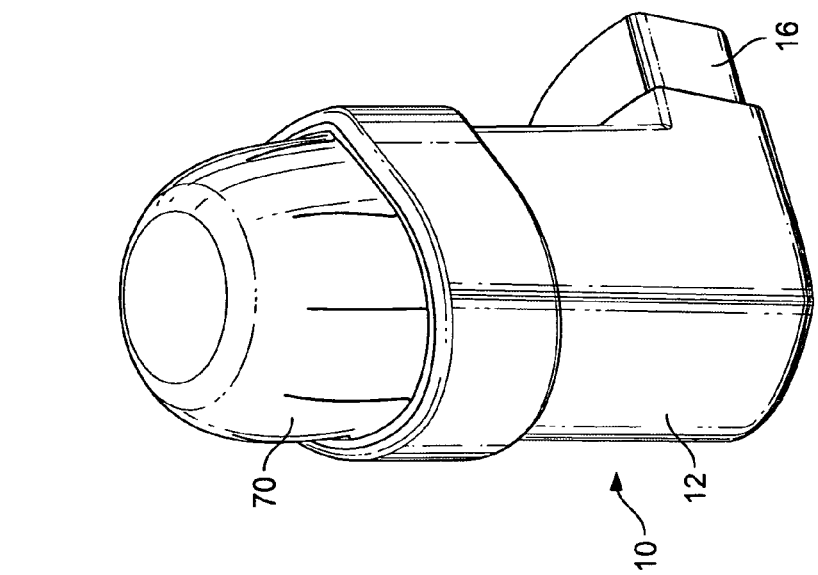
Figure 8A:
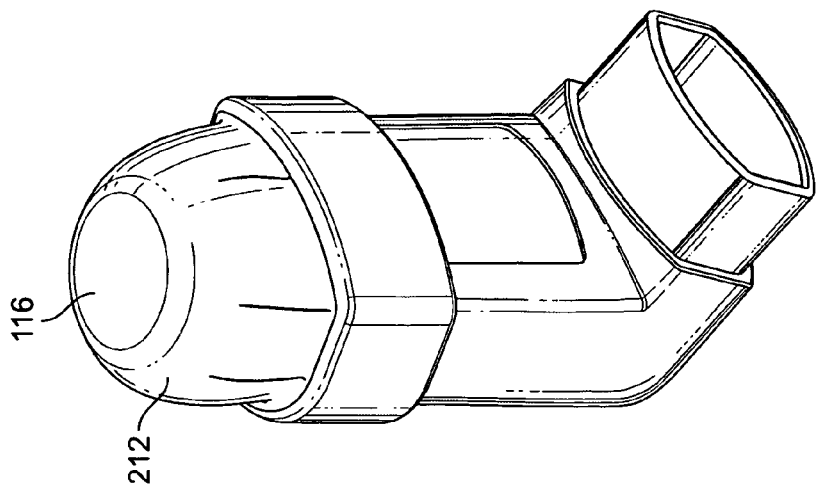
Figure 8F:
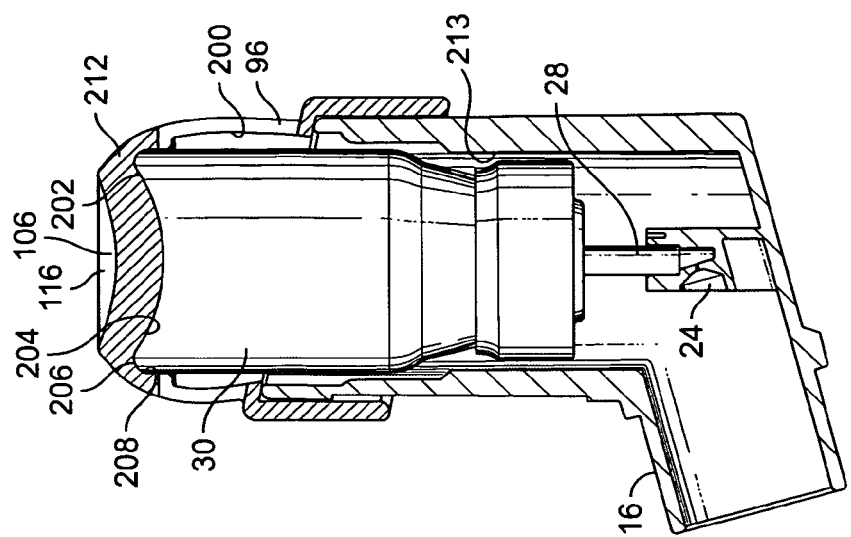
Figure 8E:
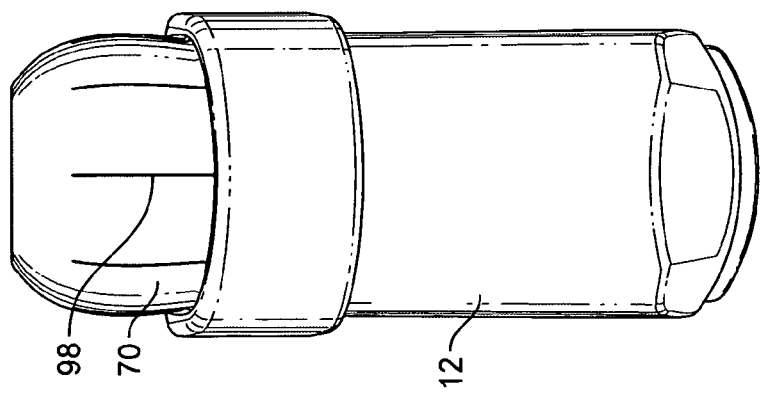
Figure 8D:
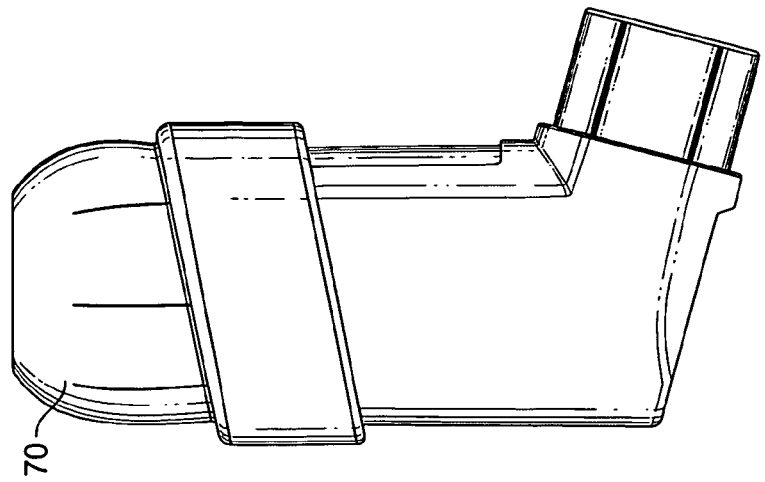
Figure 8G:
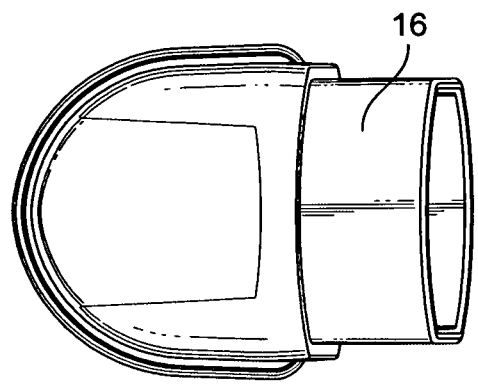
Figure 8H:
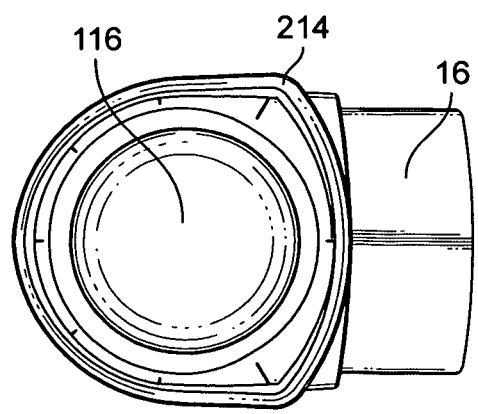

FIGS. 8A to 8H, 9 and 10A to 10C show a modification of the embodiment of FIGS. 7A to 7F. Similar components are given similar reference signs. In this embodiment, a series of eight slits 98 are spaced around the periphery of the sidewall 96. As in other embodiments, when the user starts to inhale, the air inlets formed by the slits 96 are closed and, so, no air circulates through the inhaler 10. Whilst continuing to inhale, the user pushes down on the housing cap 70 and this pushes down the canister 30 such that the air inlets 96 are opened up so that air starts flowing as soon as the drug is emitted through the valve stem 28. The housing cap 70 is essentially an adapter which can be placed on a conventional metered dose inhaler housing 10 and therefore transforms a conventional metered dose inhaler. As in other embodiments, when the user tries to inhale, the slits 96 will close even further due to the negative inhaling pressure applied to the inside of the inwardly concave inner surface 200 of the sidewall 96. As the user pushes down on the housing cap 70, the housing cap deforms, the slits 96 open up and therefore form air inlets such that air can pass down between the canister 30 and an inner wall 213 of the housing 10 towards the outlet nozzle 24 and the mouthpiece 16, as shown in FIG. 8F, which is a cross section on the plane A-A in FIG. 8C.

As shown in FIG. 8F, the generally flat top surface 106 of the housing cap 70 fits tightly around the top 202 of the canister 30. The top surface/portion 106 has a downwardly convex lower surface 204 which is dome shaped and is surrounded by a downwardly concave gutter 206 which leads to a short cylindrical sidewall portion 208. The top 202 of the canister 30 has a corresponding shape and there is therefore a tight fit between this and the dome 204, gutter 206 and short cylindrical wall portion 208 of the housing cap 70. This avoids too much play in the housing cap 70 so that it cannot easily slide sideways when pushed sideways, which could otherwise deform it and cause the air inlet slits 98 to open up slightly. The tight fitting of the parts therefore avoids this such that the slits 98 will only open when the top portion 106 of the housing cap is pushed downwardly. The lack of free space above the canister 30 and the tight fit prevent the housing cap 70 being deformable before the user pushes down on the canister.

The top portion 106 of the housing cap 70 is suffer than the sidewall 96. This prevents the top 106 of the housing cap 70 being too flexible and it is accordingly not possible to push down on the centre of the housing cap 70 without the housing cap 70 deforming properly and opening the slits 98. The extra stiffness of the top portion 106 of the adapter is provided by giving the top portion 106 greater thickness than the sidewall 96 as shown, or by using a different material for each of the top portion 106 and sidewall 96 (such as by using an in-mould double shot technique), or both concepts may be applied. The stiff top portion 106 ensures that there is good engagement between the user's finger 210 (FIG. 9) and the canister 30.

As shown in FIG. 8F, the dimple 116 creates a finger grip and this motivates the user to push the canister 30 down in the middle. A chamfer 212 which surrounds the dimple 116 reduces the size of the finger grip provided by the dimple 116 and therefore helps to align the user's finger 210 in the centre of the top portion 106 of the housing cap 70. This therefore advantageously improves the likelihood of the user pressing straight down onto the canister 30.

Figure 9:
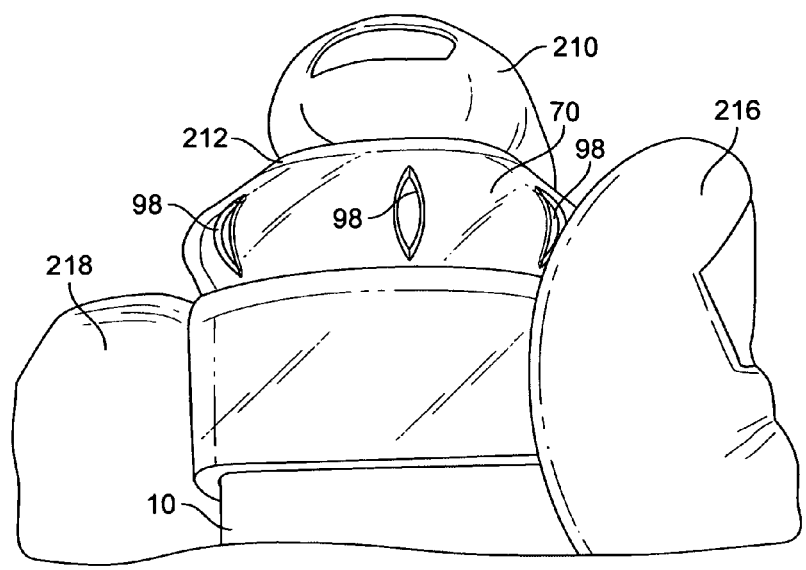
FIG. 9 shows the embodiment of FIGS. 8A to 8H in use.
Figure 10A:
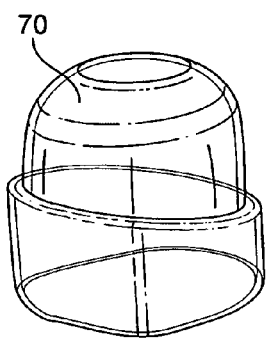
FIGS. 10A to 10C are views of the housing cap of the inhaler of FIGS. 8A to 8H.
Figure 10B:
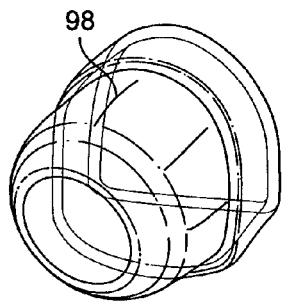
Figure 10C:
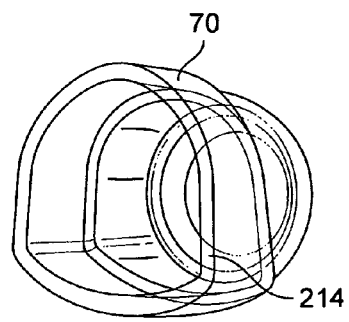

Also as shown in FIG. 8F, the sidewall 96 is slightly outwardly curved in the rest configuration of the housing cap 70. The sidewall 96 thus forms a part-spheroidal surface and the curving nature of this ensures that the sidewall 96 will always deform outwardly. In this respect, the curved surface shown in FIG. 8F is advantageous compared to a straighter surface which might sometimes locally deform inwardly. The number of the slits 98 and their relative position and spacing on the housing cap 70 can be changed in other embodiments. The inhaler 10 is not rotationally symmetrical and accordingly, the housing cap 70 needs to be oriented correctly on it. The section of the inhaler 10 can be seen in FIG. 8H and the section 214 of the housing cap corresponds to the section of the inhaler. FIG. 9 shows the housing cap 70 and inhaler 10 of FIGS. 8A to 8H in use and, here, the user is shown to be holding the housing cap 70 between thumb 216 and middle finger 218 of the right hand and the index finger 210 is shown to be pressing down on the dimple 116. At the same time, the user is inhaling through the mouthpiece 16 and, as shown in FIG. 9, the slits 98 have opened as the housing cap 70 has resiliently and reversibly deformed to the configuration shown in which the slits 98 are all open, such that airflow can pass through them and down between the canister 30 and the inner wall 213 of the housing 12 towards the mouthpiece 16. Once the user releases the pressure on the dimple 116 by releasing the index finger 210, the canister 30 and sidewall 96 and top portion 106 automatically self-return to the relaxed or rest configuration thereof shown in FIGS. 8A to 8H.

Figure 11A:
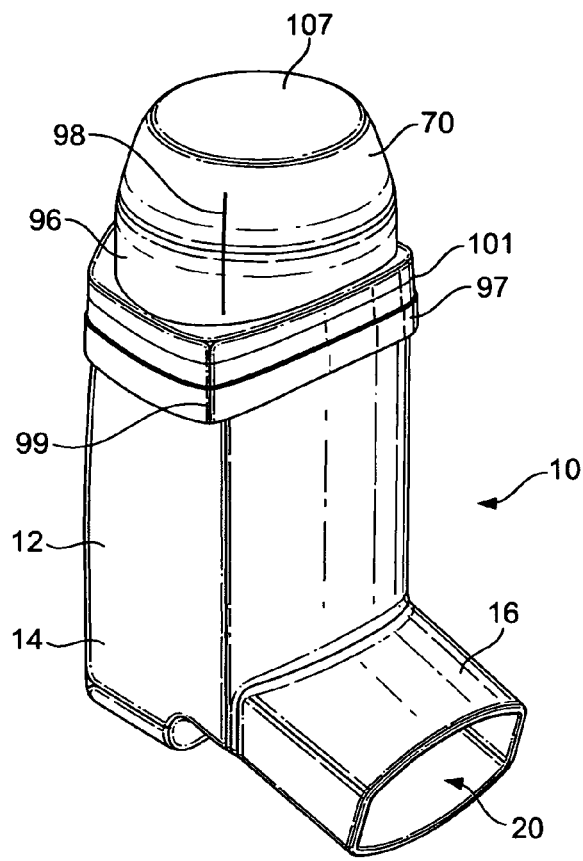
FIG. 11A shows a perspective view of a further preferred embodiment of an inhaler and housing cap in accordance with the invention.
Figure 14:
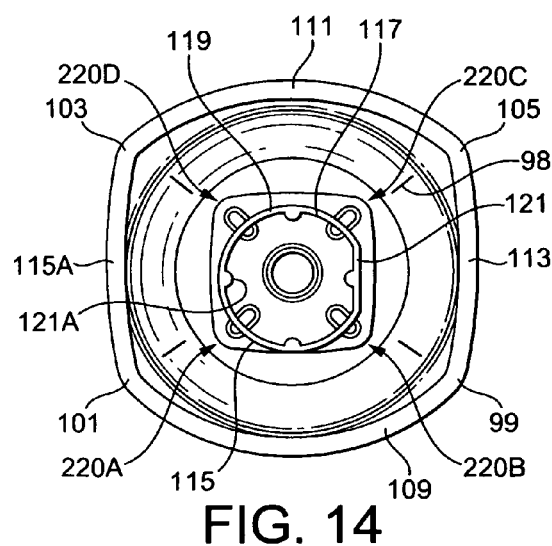

FIG. 11A onwards show a revised embodiment of inhaler 10 (a modification of the FIG. 8A embodiment) in accordance with a preferred embodiment of the present invention with a similar housing 12 having a hollow main body 14 and mouthpiece 16 with an outlet aperture 20. Similar components are given similar reference signs to those used with respect to the embodiment of FIGS. 8 A to 8H, 9 and 10A to 10C. In this embodiment, a series of four slits 98 are spaced around the periphery of the side wall 96. A skirt portion 97 of the housing cap 70 has four corners 99, 101, 103, 105, each slit 98 is substantially aligned with a respective one of the corners 99, 101, 103, 105 and each slit 98 is generally aligned with and points towards the respective corner such that the two generally fall within a common plane. For example, with reference to FIG. 14, one of these planes would be perpendicular to the page of the drawing and generally include the slit 98 and the corner 105. This configuration may be highly advantageous since the placing of the slits 98 generally at the corners 99, 101, 103, 105 allows the slits to open widely with relatively small up/down actuating movement of the generally flat top 107 of the housing cap 70. Further, each slit 98 (valve) is aligned and operably-connected to a top of the housing cap 70, where the housing cap is shaped to provide a corner 220 A, 220B, 220C, 220D, as shown in FIG. 14. Aligning the corners—or substantially aligning the corners—220A, 220B, 220C, 220D with the slits is highly advantageous since the placing of the slits 98 generally at those corners 220A, 220B, 220C, 220D allows the slits to open widely with relatively small up/down actuating movement of the top of the housing cap 70.

As described with reference to FIG. 14, the skirt arrangement 97 has front 109 and rear 111 walls as well as two side walls 113, 115A. The side walls 113, 115A are slightly curved and the distance between two front corners 99, 101 is slightly smaller than the distance between the two rear corners 103, 105 such that overall, the side walls 113, 115A taper. The side walls 113, 115A have a different curvature to the front 109 and rear 111 walls, such that the configuration of the four walls 109, 111, 113, 115A and corners 99, 101, 103, 105 only fittingly matches the similar configuration of an upper end 113 of the main body 14 of the housing 12. The skirt arrangement 97 has bilateral reflection symmetry but no rotational symmetry. This ensures that an insert component which serves as an engagement component and is fitted to an under side of the generally flat top wall 107 of the housing cap 70 is correctly positioned relative to a canister (not shown) positioned in the inhaler 10.

Figure 11B:
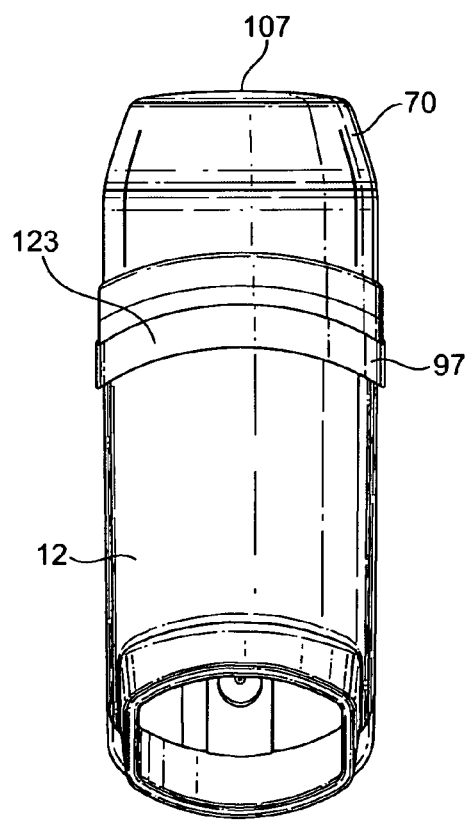
FIGS. 11B, 11C and 11D show front elevational, left elevational and sectional (looking from right) views, respectively, of the apparatus shown in FIG. 11 A.
Figure 11C:
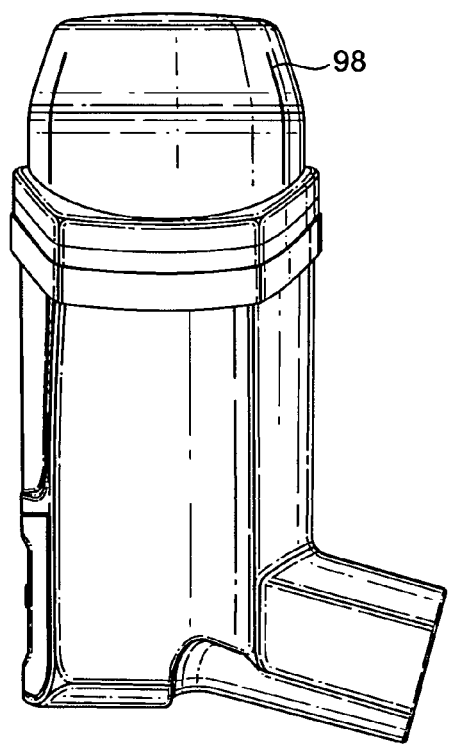
Figure 11D:
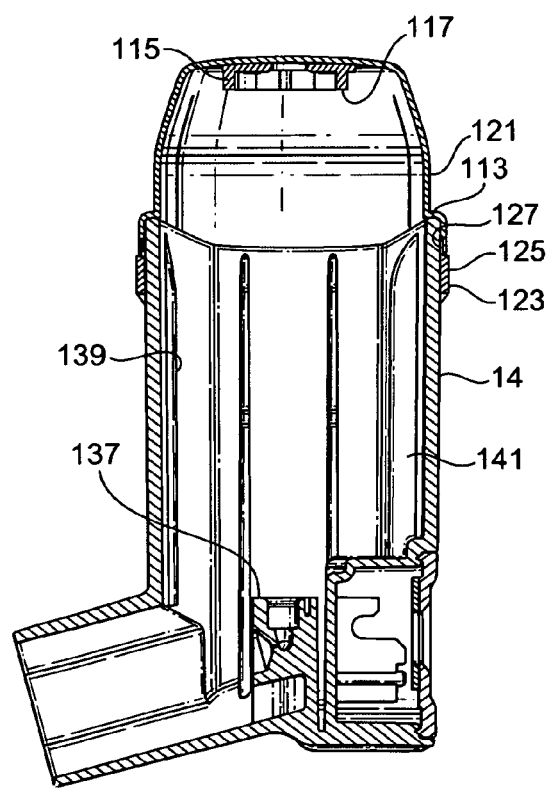
Figure 12:
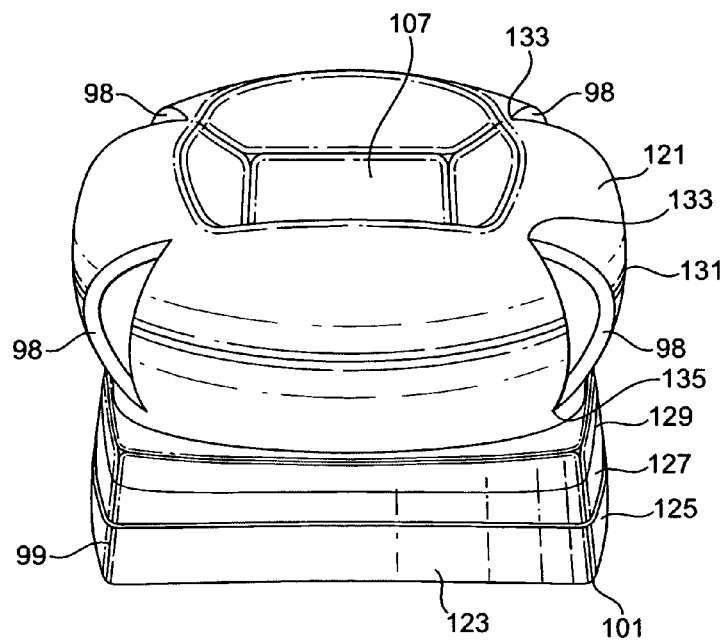
FIGS. 12, 13 and 14 show respective perspective (deformed), top plan and bottom plan views of the housing cap of FIGS. 11A to 11D.
Figure 13:
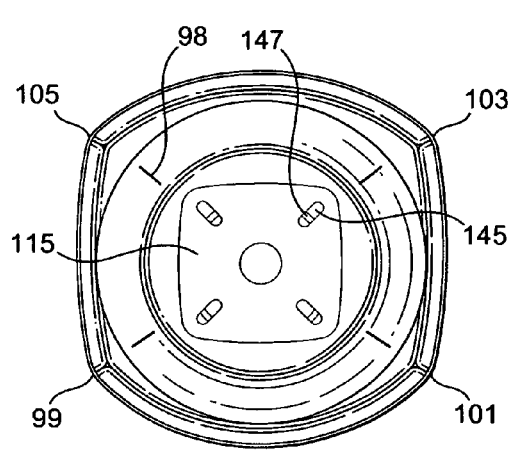

As shown in FIGS. 14 and 11D, the insert component 115 has a circumferential wall or flange 117 which is arranged to engage the canister (not shown). The circumferential wall 117 consists of a circular portion 119 extending around a majority thereof as well as a flat portion 121 forming one side thereof. The insert component 115 acts as a force spreader, ensuring that the force applied to a top of the housing cap in use is spread through all of the slits 98. As shown in FIGS. 13 and 14, the corners 220A, 220B, 220C, 220D are provided on the insert component 115. In fact, the housing cap 70 consists of three parts, namely the insert 115, a main deformable portion 121 and a skirt 123 which forms part of the skirt arrangement 97. The insert component 115 and skirt 123 are of relatively rigid material, such as an ABS, which may be designated M203. The deformable portion 121 may be significantly more flexible, such as being an ESTANE (trademark) material, such as having the X4977 designation. The deformable portion 121 may have a Shore A hardness (durometer) of 30 and other materials may be chosen instead for the three parts, such as those having hardness (durometer) in the range of 30 Shore A to 40 Shore D. As shown in FIGS. 11D and 12, the skirt 123 consists of a lower portion 125 of relatively thick material and a thinner upper portion 127 which up to line 129 in FIG. 12 is overlapped with the material of the deformable portion 121 of the housing cap 70. The rigid skirt 123 provides a good seal onto the top of the main body 14 of the inhaler.

The use of the four slits 98 located at the corners 99, 101, 103, 105 has been found to be particularly beneficial since it allows very wide opening of each slit 98 when the deformable portion 127 is deformed. As can be seen in FIG. 12, this configuration allows bowed portions 131 of the deformable portion 121 to be formed between the slits 98, each bowed portion 131 (there are four of them) extending between respective top 133 and bottom 135 ends of two adjacent ones of the slits 98. Due to the configuration with the slits 98 at the corners of the deformable portion 121 and of the skirt arrangement 97, these bowed portions 131 can deform substantially away from their original configuration to one in which the bowed portions 131 are each generally part-cylindrical as shown in FIG. 12 where the slits 98 are opened very wide therefore enabling substantial airflow across the housing cap 70 without a significant resistance or pressure drop.

The flat portion 121 of the wall 117 enables the insert component 115 to be positioned and pushed correctly down on the canister (not shown) since as shown by the valve stem block 137 position and the relative sizes of front 139 and rear 141 canister-stabilising flanges in the main body 14, the canister does not sit absolutely centrally in the main body 14. It will be appreciated that the canister is of the pressurised type having a valve stem similar to that shown in FIGS. 1A and 1B. The various components are configured such that the wall 117 in the rest position of the system, is positioned against or just spaced slightly from the top surface (not shown) of the canister (not shown).

The flexible and naturally deformable, deformable portion 121 is moulded to have a rest configuration thereof as shown in 11A and will return to this position automatically once released from a depressed configuration shown in FIG. 12. In the rest configuration, the slits 98 are surrounded by relatively continuous surfaces of the sidewall/deformable portion 121 such that fluff and debris cannot easily build up near the slits 98 where they could be at risk of undesirable inhalation. Furthermore, the very prominent position of the slits 98 both visually and from a tactile/touch perspective at the time of inhalation mean that any debris or fluff can easily be seen or felt by the user before inhalation and removed. The inhaler 10 can also be provided with a mouthpiece cap (not shown) such that debris, fluff and small insects etc cannot easily enter the inhaler 10 either near the outlet 20 or in the region of the slits 98 when the inhaler is not being used. However, the highly-openable nature of the slits and the good timing of drug deliver relative to inhalation enable the provision of an inhaler which is extremely reliable and effective. The deformable portion 121 may be relatively smooth on its outer surfaces including the generally flat top 107 or may be roughened. Roughening may allow the deformable portion 121 to be easily removed from a mould when it is moulded and may also provide grip. As shown in FIG. 1 ID, the deformable portion 121 is formed with generally a constant thickness but the flat top 107 is significantly stiffened by the insert 115 over which the deformable portion's material extends.

Instead of having one or more curved lower edges as shown in FIG. 11B, the skirt 123 may have a different shape in side elevation, such as by being generally straight when viewed from each of front, back, right and left elevations. The top of the main body 14 of the inhaler may be similarly configured for good sealing between the two.

The deformable portion 121 is of a clear material and the skirt 123 and insert component 115 may be clear or coloured. In the present embodiment, the insert component 115 is visible through the deformable portion 121 as shown in FIG. 13. The insert component 115 includes four apertures 145 near corners thereof and the deformable portion 121 may be moulded on to the insert component 115 with some material 147 of the deformable portion 121 passing into or through the apertures 145 to provide a bonding or riveting effect so as to hold the two components together. The deformable portion 121 can be moulded on to the skirt 123 in the same moulding step.

Once the housing cap has initially been moulded, the slits 98 may be formed while the deformable portion 121 is held on a mandrel (not shown). A blade (not shown) or four blades (one for each slit 98) may be pushed into the mandrel through the deformable portion 121 so as to form the slits 98.

The wall 117, in addition to the circular portion 119 and flat portion 121 may include four buttress portions 121 A which may provide additional strength and are also useful during demoulding since injector pins (not shown) in a mould (not shown) may be located directly beneath or adjacent the buttresses 121A. In an alternative, corners corresponding to 220A, 220B, 220C, 220D of the insert component 115 may be integrally formed as part of the housing cap.

Various modifications may be made to the embodiments described without departing from the scope of the invention as defined by the accompanying claims as interpreted under Patent Law.

The invention claimed is:

1. A housing cap apparatus for an inhaler, the housing cap apparatus having one or more valves for selectively restricting air flow through an air flow passageway of an inhaler,
wherein the housing cap apparatus further comprises a head portion at least partly formed of deformable material, and
wherein the valve comprises at least one sealing aperture which is deformable between a closed configuration and an open configuration, and the sealing aperture comprises an elongate sealing slit that is formed in a sidewall of the head portion.

2. Apparatus as claimed in claim 1, the deformable material being deformable between a first configuration in which the valve is restricted and a second configuration in which the valve is open for allowing air flow through the air flow passageway of the inhaler.

3. Apparatus as claimed in claim 1 in which the head portion is configured for self-closing the sealing aperture to the closed configuration and self-returning the head portion to a rest configuration.

4. Apparatus as claimed in claim 1, in which the sidewall is generally at least part-cylindrical or at least part-conical when the sealing slit is in the closed configuration.

5. Apparatus as claimed in claim 1, in which the sidewall has a curved outwardly convex cross-section when the sealing slit is closed.

6. Apparatus as claimed in claim 1, in which the housing cap includes at least one corner and in which at least one said sealing slit is located substantially adjacent and/or aligned extending substantially towards the corner.

7. Apparatus as claimed in claim 6, which includes a series of said sealing slits arranged around the sidewall.

8. Apparatus as claimed in claim 7 in which four said sealing slits and four said corners are provided.

9. Apparatus as claimed in claim 1, in which, when the sealing slit is closed, the head portion has a generally flat top and the sealing slit is oriented generally parallel to an axis perpendicular to the generally flat top.

10. Apparatus as claimed in claim 9 in which the generally flat top is relatively rigid compared to the sidewall.

11. Apparatus as claimed in claim 10, in which the generally flat top is of thicker material than the sidewall, and/or formed at least partly of stiffer material than the sidewall.

12. Apparatus as claimed in claim 10 in which the generally flat top includes an insert formed of stiffer and/or harder material than material of the sidewall.

13. Apparatus as claimed in claim 1 in which the sidewall has a Shore A hardness of about 30.

14. Apparatus as claimed in claim 9 in which the flat top has a Shore D hardness of about 40 or less.

15. Apparatus as claimed in claim 9 in which the flat top has a Shore A hardness of about 85.

16. Apparatus as claimed in claim 1 in which the sidewall is arranged to adopt a deformed bulging configuration when the sealing slit is in the open configuration.

17. Apparatus as claimed in claim 1 in which the head portion has an engagement portion arranged to engage, move and fire a metered dose canister.

18. Apparatus as claimed in claim 17 in which the engagement portion comprises a component, the component having a wall or flange of at least partly circular form for engaging the metered dose canister.

19. Apparatus as claimed in claim 1 in which the housing cap apparatus includes a skirt arrangement arranged to sealingly engage a housing of an inhaler.

20. Apparatus as claimed in claim 19 in which the skirt arrangement includes a stiffening portion, the stiffening portion having greater stiffness and/or hardness (durometer) than a sidewall portion of the housing cap apparatus.

21. Apparatus as claimed in claim 19 in which the skirt arrangement has a shape arranged to fittingly match a similarly-shaped end of an inhaler housing in only one relative angular configuration.

22. Apparatus as claimed in claim 1, wherein the valve is operably-connected to a top of the housing cap apparatus such that depression of the top of the housing cap apparatus opens the valve from a closed, rest position.

23. Apparatus as claimed in claim 22, wherein the top of the housing cap apparatus is shaped to provide a corner aligned, adjacent or otherwise in communication with the valve, to facilitate opening of the valve.

24. Apparatus as claimed in claim 22, wherein the top of the housing cap apparatus comprises an insert providing a corner aligned, adjacent or otherwise in communication with the valve, to facilitate opening of the valve.

25. Apparatus as claimed in claim 23, comprising a corner per valve.

26. An inhaler for inhalation into the airway of a user, the inhaler having a housing at least partially defining the air flow passageway extending through the inhaler from an air inlet to an outlet, the inhaler including the housing cap apparatus as claimed in claim 1.

27. An inhaler for inhalation into the airway of a user, the inhaler having a housing at least partially defining an air flow passageway extending through the inhaler from an air inlet to an outlet, wherein at least one valve is provided for selectively restricting the flow passageway,
wherein the valve includes a sealing ring arranged to selectively form a seal between a metered dose canister and an inner wall of the housing, the sealing ring having a central opening through which at least a portion of the metered dose canister is positioned; and
wherein the sealing ring is flexible and is arranged to deform from a closed configuration to an open configuration in which the sealing ring permits air flow along the air flow passageway.

28. An inhaler as claimed in claim 27, comprising a housing cap apparatus having a housing cap valve for selectively restricting air flow through the air flow passageway of the inhaler.

29. An inhaler as claimed in claim 28, the housing cap apparatus having a deformable portion formed of deformable material and including the housing cap valve, the deformable portion being deformable between a first configuration in which the housing cap valve is restricted and a second configuration in which the housing cap valve is open for allowing air flow through the air flow passageway.

30. An inhaler as claimed in claim 29 in which the deformable portion comprises at least part of the housing cap apparatus.

31. An inhaler as claimed in claim 27, in which the outlet comprises an aperture in a mouthpiece of the housing.

32. An inhaler as claimed in claim 27, in which the housing has a canister-receiving portion arranged to receive the metered dose canister.

33. An inhaler as claimed in claim 32, which includes the metered dose canister arranged to be located in the canister-receiving portion, the canister having a main body which is movable in the canister-receiving portion for firing a metered dose of drug into the flow passageway.

34. An inhaler as claimed in claim 33 in which the metered dose canister has a stem extending from the main body and a metering valve, the main body being pressurised and movable relative to the valve stem for firing the metered dose via the metering valve.

35. Apparatus as claimed in claim 1, wherein the valve is fully closable for fully preventing air flow.

36. Apparatus as claimed in claim 1, in which the valve is operable in response to a manual operation so as to permit air flow.

37. An inhaler as claimed in claim 33 in which the canister and the valve are arranged for coordinated opening of the valve and firing of the metered dose in response to a manual operation, the canister being movable in the housing in response the manual operation.

38. An inhaler as claimed in claim 27, which includes a housing cap apparatus arranged to fit on the housing, at least part of the housing cap being movable relative to the housing for opening and closing the valve.

39. An inhaler as claimed in claim 38 in which the housing cap apparatus has a skirt arranged to sealingly fit the housing.

40. An inhaler as claimed in claim 27 including the metered dose canister located in the housing, the canister having a cylindrical surface arranged to selectively seal inside the sealing ring, the canister having a neck portion of smaller cross-dimension than the cylindrical surface and being slidable in the housing for placing the neck portion adjacent the sealing ring and spaced inwardly therefrom so as to open the valve.

41. An inhaler as claimed in claim 27, which includes a steadying ring located in the housing and arranged to steady the metered dose canister inside the housing.

42. An inhaler as claimed in claim 26, in which the housing has at least one aperture formed in an outer wall thereof, the housing cap apparatus being movable relative to the housing to place the sealing aperture of the valve and the aperture of the outer wall in and out of register with one another for opening and closing the valve, respectively.

43. Apparatus as claimed in claim 9 in which the generally flat top includes a central concave finger grip.

44. Apparatus as claimed in claim 43 in which the finger grip is surrounded by a chamfer.

45. Apparatus as claimed in claim 9, in which the generally flat top has a lower surface thereof arranged to mate on top of a metered dose canister.

46. Apparatus as claimed in claim 45, in which the lower surface has a downwardly convex central dome surrounded by a concave annular gutter leading to a downwardly extending cylindrical wall portion of the generally cylindrical flat top.

47. Apparatus as claimed in claim 1, which includes a skirt arranged to sealingly engage a housing of the inhaler.

48. Apparatus as claimed in claim 1, in which the housing cap apparatus is arranged to be connectable to an inhaler housing by provision of mutually engaging threads which permit a threaded twisting removal or connection thereof.

* * * * *